United States Patent
Tong et al.

(10) Patent No.: US 11,286,506 B2
(45) Date of Patent: Mar. 29, 2022

(54) TYPE I-B CRISPR-CAS SYSTEM GENE CAS3-BASED GENE EDITING METHOD

(71) Applicant: ANHUI UNIVERSITY, Hefei (CN)

(72) Inventors: Wangyu Tong, Shanghai (CN); Yanyan Tang, Huaibei (CN); Tingting Xia, Lu'an (CN)

(73) Assignee: ANHUI UNIVERSITY, Hefei (CN)

( * ) Notice: Subject to any disclaimer, the term of this patent is extended or adjusted under 35 U.S.C. 154(b) by 483 days.

(21) Appl. No.: 16/487,443

(22) PCT Filed: Jul. 24, 2018

(86) PCT No.: PCT/CN2018/096774
§ 371 (c)(1),
(2) Date: Aug. 21, 2019

(87) PCT Pub. No.: WO2019/056848
PCT Pub. Date: Mar. 28, 2019

(65) Prior Publication Data
US 2019/0376089 A1    Dec. 12, 2019

(30) Foreign Application Priority Data

Sep. 19, 2017  (CN) .......................... 201710847193.8

(51) Int. Cl.
| C12N 15/90 | (2006.01) |
| C12N 9/22 | (2006.01) |
| C12N 15/11 | (2006.01) |
| C12N 15/63 | (2006.01) |

(52) U.S. Cl.
CPC ............ *C12N 15/907* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

FOREIGN PATENT DOCUMENTS

| CN | 105505976 A | 4/2016 |
| CN | 105543266 A | 5/2016 |
| CN | 106755037 A | 5/2017 |
| CN | 106834323 A | 6/2017 |
| CN | 107557373 A | 1/2018 |

OTHER PUBLICATIONS

Yong, Dexiang. CRISPr-Cas System in Streptomyces Virginiae IBL14 and Its Gene Editing Method. China Master's Theses Full-Text Database, Dec. 31, 2016, ISSN:1674-0246.
Y. Li, et al. Harnessing Type I and Type III CRISPR-Cas Systems for Genome Editing. Nucleic Acids Research 2016, vol. 44, No. 4, e34.
O.O.Abudayyeh, et al. C2c2 is a Single-Component Programmable RNA-Guided RNA-Targeting CRISPR Effector. Science Aug. 5, 2016, vol. 353 Issue E-6299, pp. 5573.
D. Burstein et al. New CRISPR-Cas Systems from Unculticated Microbes. Nature, Feb. 9, 2017, vol. 542, pp. 237-241.
P.Mohanraju, et al. Diverse Evolutionary Roots and Mechanistic Variations of the CRISPR-Cas Systems. Science Aug. 5, 2016, vol. 353, Issue 6299, pp. 5147.
S.Shmakov, et al. Diversity and Evolution of Class 2 CRISPR-Cas Systems. Nat Rev Microbiol, Mar. 2017, 15(3), pp. 169-182.
F. Q. Wang, et al. New Microbiological Transformations of Steroids by Streptomyces Virginiaee IBL-14. Environmental Science &Technology 2009, vol. 43, No. 15, pp. 5967-5974.
E.Kim, et al. In Vivo Genome Editing with a Small Cas9 Orthologue Derived from *Campylobacter Jejuni*. Nat Commun 2017, (8) 14500.
R.D. Fagerlund, et al. The Cpfl CRISPR-Cas Protein Expands Genome-Editing Tools. Genome Biol 2015, (16) 251.

*Primary Examiner* — Suzanne M Noakes
*Assistant Examiner* — Jae W Lee
(74) *Attorney, Agent, or Firm* — Bayramoglu Law Offices LLC

(57) ABSTRACT

A novel gene editing system developed based on the gene cas3 in the type I-B CRISPR-Cas system in the chromosome of *Streptomyces virginiae* IBL14 enables the gene editing of a type I CRISPR-Cas system on biological cell genomes for the first time. In the system, Cas3 can specifically cleave a DNA fragment of interest guided by crRNA or t-DNA. The new approach can be applied to rapid, simple and correct genome editing of prokaryotic and eukaryotic cells, which provides novel supplements and selections for the commercialized gene editing system developed based on Cas9 in type II.

9 Claims, 3 Drawing Sheets
Specification includes a Sequence Listing.

(A)      (B)
C: control-*E. coli* JM109 (DE3); G: gene-edited mutant-*E. coli* JM109 (DE3)-Δ*lacZ*; L: ladder

TYPE I-B CRISPR-CAS SYSTEM GENE CAS3-BASED GENE EDITING METHOD

CROSS REFERENCE TO THE RELATED APPLICATIONS

This application is the national phase entry of International Application No. PCT/CN2018/096774, filed on Jul. 24, 2018, which is based upon and claims priority to Chinese Patent Application No. 201710847193.8, filed on Sep. 19, 2017, the entire contents of which are incorporated herein by reference.

TECHNICAL FIELD

The present invention relates to gene editing technology in the technical field of biology, and more specifically to a gene editing method based on a gene cas3 in a type I-B CRISPR-Cas system.

BACKGROUND

A CRISPR-Cas system widely exists in archaea and bacterial genomes. The currently discovered CRISPR-Cas system is divided into two classes that are subdivided into six types: class 1 in interference phase generates an effector complex with multiple Cas proteins, including type 1, III and IV; class 2 is a single Cas protein for interference, including type II, V and VI; type I to VI respectively take Cas3, Cas9, Cas10, undetermined, Cpf1 and C2c2 as signature proteins (P. Mohanraju, K S Makarova, B. Zetsche, F. Zhang, E V Koonin, J. van der Oost, Diverse evolutionary roots and mechanistic variations of the CRISPR-Cas systems. Science 2016, (353) 5147). Wherein type I is the most extensive, accounting for 60% or above of the identified. Unfortunately, although many type I CRISPR-Cas systems have been discovered, there are no reports that they can be applied to gene editing. In particular, the gene editing performed by DNA guiding has not been reported.

Despite there are reports that the extremely thermophilic *Sulfolobus islandicus* can use its own type I and type II CRISPR-Cas systems to perform gene editing on its own genome through a gene editing vector (Y. Li, S. Pan, Y. Zhang, M. Ren, M. Feng, N. Peng, L. Chen, Y. X. Liang, Q. She, Harnessing Type I and Type I CRISPR-Cas systems for genome editing. Nucleic acids research 2016, (44) e34-e34); a C2c2 protein in *Leptotrichia shahii* can specifically knock out an mRNA (O. O. Abudayyeh, J. S. Gootenberg, S. Konermann, J. Joung, I. M. Slaymaker, D. B. Cox, S. Shmakov, K. S. Makarova, E. Semenova, L. Minakhin, K. Severinov, A. Regev, E. S. Lander, E. V. Koonin, F. Zhang, C2c2 is a single-component programmable RNA-guided RNA-targeting CRISPR effector. Science 2016 (e353) aaf5573); CasX and CasY, which may be used for gene editing, have been discovered in metagenomics (D. Burstein, L. B. Harrington, S. C. Strutt, A. J. Probst, K. Anantharaman, B. C. Thomas, J. A. Doudna, J. F. Banfield, New CRISPR-Cas Systems from uncultivated microbes. Nature 2017, (542) 237-241). However, it has been currently confirmed that only class 2 type II Cas9 (*Streptococcus pyogenes, Campylobacter jejuni*, etc.) and type V Cpf1 (*Acidaminococcus* sp. BV3L6 and Lactospiraceae bacterium MA2020) can perform gene editing on other biological genomes (P. Mohanraju, K. S. Makarova, B. Zetsche, F. Zhang, E. V. Koonin, J. van der Oost, Diverse evolutionary roots and mechanistic variations of the CRISPR-Cas systems. Science 2016, (353) aad5147; S. Shmakov, A. Smargon, D. Scott, D. Cox, N. Pyzocha, W. Yan, O. O. Abudayyeh, J. S. Gootenberg, K. S. Makarova, Y. I. Wolf, K. Severinov, F. Zhang, E. V. Koonin, Diversity and evolution of class 2 CRISPR-Cas systems. Nat Rev Microbiol 2017, (15) 169-182). At present, the gene editing tools constructed based on cas9 (single gene system) in the type II CRISPR-Cas system are still mainly and commercially used for gene editing.

*Streptomyces virginiae* IBL14 is a strain isolated and purified in the laboratory that can grow using a variety of steroidal compounds as a sole carbon source; it is the only microorganism that has been reported so far to enzymatically catalyze the F-ring (C25 hydroxylation) of diosgenin (the main raw material of steroidal drugs) to react (F.-Q. Wang, C.-G. Zhang, B. Li, D.-Z. Wei, W.-Y. Tong, New microbiological transformations of steroids by *Streptomyces virginiae* IBL-14. Environmental science & technology 2009, (43) 5967-5974). The whole genome sequencing and bioinformatics analysis of the strain IBL14 reveal that there is a type I-B-Svi CRISPR-Cas system in this strain. In particular, the system can perform gene editing on its own genome through a gene editing vector (consisting of a guide DNA fragment/g-DNA and a template DNA fragment/t-DNA) (CN201510999333.4, CN201511002817.3); and an editing tool constructed based on cas7-5-3-4-1-2 (6-gene system) and cas7-5-3 (3-gene system) in the system can effectively perform gene editing on prokaryotic genomes (CN201611113137.3, CN201611089333.1).

In class 2 CRISPR-Cas system, SpCas9 in type II (4107 nt) (http://www.ncbi.nlm.nih.gov), CjCas9 (2955 nt) in type II (E. Kim, T. Koo, S W Park, D. Kim, K. Kim, H Y Cho, D. W. Song, K. J. Lee, M H. Jung, S. Kim, J. H. Kim, J. S. Kim, In vivo genome editing with a small Cas9 orthologue derived from *Campylobacter jejuni*. Nat Commun 2017, (8) 14500), and Cpf1 in type V (3924 nt) (R D. Fagerlund, R H. Staals, P. C. Fineran, The Cpf1 CRISPR-Cas protein expands genome-editing tools. Genome Biol 2015, (16) 251) have such disadvantages as large molecular weights which are unsuitable for carring of most vectors (such as viruses and plasmids), off-target and so on, therefore, the present invention will disclose a gene editing system consisting of a Cas3 expression vector (vector-cas3) and a gene editing vector (vector-t/g-gene abbreviation) designed based on a gene cas3 (single gene system) in a type I-B CRISPR-Cas system in a chromosome of *Streptomyces virginiae* IBL14. The gene editing system, for the first time, enables gene editing on prokaryotic and eukaryotic genomes based on a single Cas3 protein in a Type I CRISPR-Cas system. In particular, the protein SviCas3 can perform DNA cleavage by crRNA guiding or by t-DNA localization; and the molecular weight of the protein SviCas3 (2316 nt/771 aa) is much smaller than the molecular weights of a commercial protein SpCas9 (1368 aa) and the smallest protein CjCas9 (984 aa). The RNA- and/or DNA-guided genome editing in the strain IBL14 itself and other organisms is characterized with high efficiency, error-free and no off-target.

SUMMARY

Problem Solutions

Technical Solutions

The technical problem to be solved by the present invention is to provide a tool for performing gene editing on prokaryotic and eukaryotic genomes based on a single Cas3 protein in a type I-B CRISPR-Cas system.

For this purpose, the technical solution adopted by the present invention is as follows:

A gene editing method based on the gene cas3 (as shown in SEQ ID NO: 1) in the type I-B-Svi CRISPR-Cas system of *Streptomyces virginiae* IBL14 is characterized by comprising the step of performing gene editing on genetic materials of all organisms by using a set of gene editing tools consisting of a protein Cas3 (as shown in SEQ ID NO: 2) expression vector and a gene editing vector with a template DNA (t-DNA) and/or a guide DNA (g-DNA).

The gene editing method based on the gene cas3 in the type I-B CRISPR-Cas system is characterized by comprising the following steps:

(1) Construction of Cas3 Expression Vector

Designing primers based on the sequence information of the gene cas3 in *Streptomyces virginiae* IBL14, using a *Streptomyces virginiae* IBL14 genome as a template, amplifying to obtain the gene cas3 by a PCR reaction, and ligating to a vector to obtain the Cas3 expression vector:

(2) Construction of Gene Editing Vector

Designing primers according to the gene sequence of interest, using a biological genome of interest as a template, designing and synthesizing a t-DNA fragment with desired genetic function consisting of upstream and downstream homologous arms of the gene of interest by PCR;

Designing and chemically synthesizing a g-DNA fragment sequentially consisting of a restriction site, a transcription promoter, a crDNA for transcribing a crRNA, a transcription terminator, and a restriction site according to the sequence information of biological target gene; and Respectively ligating the prepared t-DNA fragment and g-DNA fragment to a vector to obtain the gene editing vector;

(3) Construction and Validation of Gene Edited Recombinant

Preparing competent cells or protoplasts, and introducing the cas3 expression vector obtained in step (1) and the gene editing vector obtained in step (2) into the competent cells or the protoplasts to obtain the gene-edited recombinant; performing PCR and DNA sequencing and/or functional analysis on a recombinant chromosomal gene to confirm the gene-edited recombinant.

The Cas3 expression vector refers to a nucleic acid vector such as a plasmid or a virus and a DNA sequence capable of expressing Cas3, which is chemically and biologically synthesized.

The t-DNA refers to a chemically and biologically synthesized t-DNA fragment with desired genetic function, which is respectively combined with the Cas3 expression vector or the gene editing vector or exists independently.

The g-DNA refers to a chemically or biologically synthesized g-DNA fragment capable of transcribing to obtain a crRNA, and the fragment can respectively bind into the Cas3 expression vector or the gene editing vector.

The genetic materials of all organisms refer to genetic materials originated from prokaryotic cells, or eukaryotic cells, or/and viruses without cellular structures.

The gene editing refers to such a genome editing that is mediated through specific cleavage of Cas3 on a target DNA guided by crRNA or t-DNA.

The gene editing refers to deletion, insertion, scarless point mutation, and any combination performed on biological genetic materials.

Beneficial Effects of the Invention

Beneficial Effects

The present invention provides a novel gene editing system developed based on the gene cas3 in the type I-B CRISPR-Cas system in the chromosome of the *Streptomyces virginiae* IBL14, which enables the gene editing of the type I CRISPR-Cas system on biological cell genomes for the first time, and provides new supplements and selections for the gene editing system developed by type II commercialized Cas9. In this system, SviCas3 can specifically cleave the target DNA guided by crRNA or t-DNA. The system can be applied to perform error-free, simple and rapid gene editing on prokaryotic and eukaryotic genomes. The optimized gene editing system based on SviCas3 is expected to be superior to the commercialized gene editing system constructed based on SpCas9 in many fields due to its small molecular weight and guiding by DNA.

DETAILED DESCRIPTION OF THE EMBODIMENTS

Optimal Embodiment for Implementing the Invention

Optimal Embodiment

EMBODIMENTS

Figure 1:
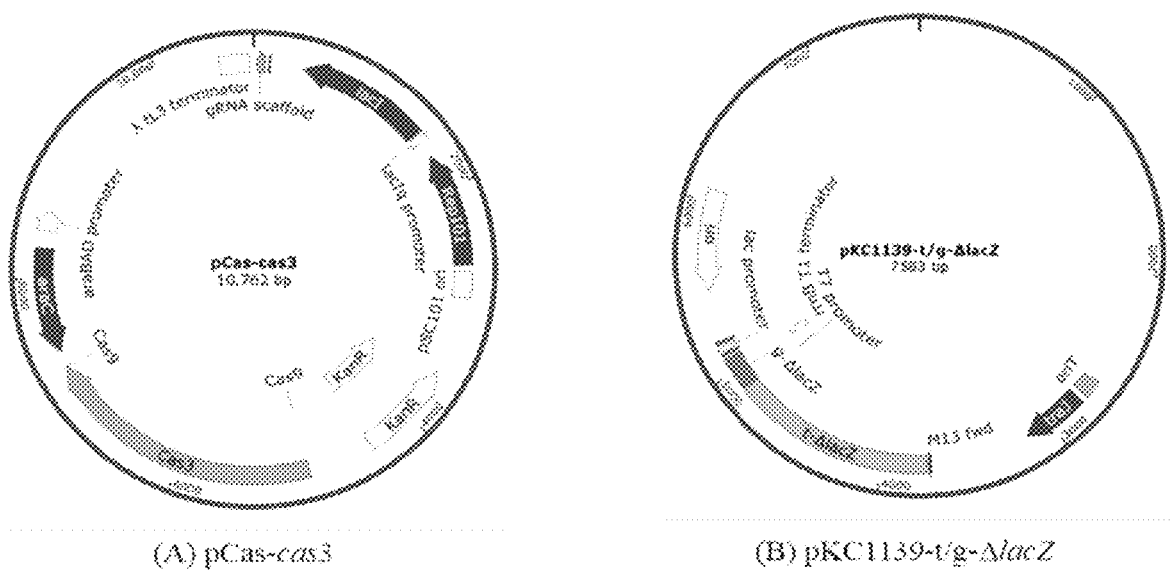
FIG. 1 shows pCas-cas3 and pKC1139-t/g-ΔlacZ construction diagrams. (A) is a Cas3 expression vector pCas-cas3, containing a Cas3 protein gene and a kanamycin (Kan$^R$) resistant gene; (B) is a gene editing vector pKC1139-t/g-ΔlacZ, containing a template DNA fragment of t-ΔlacZ and a guide DNA fragment of g-ΔlacZ.

In order to more fully understand the technical contents of the present invention, the technical solutions of the present invention are further described and illustrated in conjunction with the specific embodiments, which are intended to better explain the contents of the present invention. The following embodiments do not limit the scope of protection of the present invention. In addition, the following materials are used in the listed embodiments unless otherwise stated:

1) Strains and Vectors

TABLE 1

| Names | Characteristics |
| --- | --- |
| Strains | |
| *S. virginiae* IBL14/SV IBL14 | wild |
| *E. coli* DH5α/EC DH5α | F', φ80dlacZΔM15, Δ(lacZYA-argF)U169, deo R, rec A1, end A1, hsd R17(rk⁻, mk⁺), pho A, sup E44, λ--, thi-1, gyr A96, rel A1 |
| EC DH5α-pKC1139 | pKC1139 |
| EC DH5α-pKC1139-t/g-ΔlacZ | pKC1139-t/g-lacZ |
| EC DH5α-pCas | pCas |
| EC DH5α-pCas-cas3 | pCas-cas3 |
| EC DH5α-pRS415-cas3 | pRS415-cas3 |
| EC DH5α-pYES2-NTA-t/g-crtE | pYES2-NTA-t/g-crtE |
| EC JM109 (DES) | end A1, recA1, gyrA96, thi-1, hsd/R17 (rk⁻, mk⁺), relA1, supE44, Δ(lac-proAB)/[F', traD36, proAB, lacI^qZΔM15], λpKCl139, 1DE3 |
| EC JM109 (DE3)-pKC1139 | pKC1139 |
| EC JM109 (DE3)-pCas | pCas |
| EC JM109 (DE3)-pCas-cas3 | pCas-cas3 |
| EC JM109 (DE3)-ΔlacZ | ΔlacZ |
| *B. subtilis* 168/BS 168 | trp C2 |
| BS 168-Δldh:: cat | Δldh:: cat |
| *Saccharomyces cerevisiae* BY4741/SC BY4741 | ΔhoI:: crtE:: crtY:: crtI:: crtB, ΔMet, ΔHis, ΔLeu, ΔUra |
| 5C BY4741-pRS415-cas3 | pRS415-cas3 |
| SC BY4741-ΔcrtE | ΔcrtE |
| HEK293 | Easy transfection, Expression cell |
| HEK293-Δdrosha:: hyg | Δdrosha:: hyg |
| Vectors | |
| pKC1139 | Expression vector in *Streptomyces*, Apramycin^R, oriT, lac promoter |
| pKC1139-t/g-ΔlacZ | t/g-ΔlacZ |
| pCas | lambda-Red recombinase expression plasmid, Kan^R, ParaB promoter, ori:repA101ts |
| pCas-cas3 | cas 3 |
| pHT304 | Expression/Shutter Vector in *E. coli*/*B. subtilis*, Amp^R/Erm^R, lac promoter |
| pHT304-cas3 | cas 3 |
| pCAS9-BFP empty | Expression Vector in Mammalian. Amp^R, U6 promoter, CMV enhancer |
| pCAS9-BFP-cas3 | cas 3 |
| pRS415 | Shutter Vector, Amp^R, Leu2 |
| pRS415-cas3 | cas3 |
| pYES2 | Expression, Amp^R, gal1 promoter, Galaclose induction, high copy number |
| pYES2-t/g-crtE | t/g-crtE |
| pUC19 | pBR322 origin, Amp^R, lac_promoter, lacZ_a |
| pUC19-t/g-Δdrosha:: hyg | t/g-Δdrosha:: hyg |
| pSilencer2.1-U6 hygro | U6 pomoter, AmpR, HygR, ColE1 origin |
| pRS415-cas9 | Expression/Shutter Vector in *E. coli*/ *S. cerevisiae*, AmpR, gal1 promoter |

2) Buffer Solution and Medium 400 mL of LiAc/DTT/TE Buffer Solution 4.088 g of LiAc.2H$_2$O (0.1 M), 0.48456 g of Tris (10 mM, pH 7.5), 0.1169 g of EDTA (1 mM), and 300 mL of ddH$_2$O were dissolved, with pH adjusted to 7.5 by HCl, were diluted to 400 mL, and sterilized at a temperature of 115° C. for 30 min, 0.617 g of DTT was added after being filtered and sterilized in 5 ml of distilled water.

LB Medium 5 g of yeast powder, 10 g of peptone, and 10 g of NaCl were dissolved by adding an appropriate amount of tap water, and then diluted to 1 L, with pH adjusted to 7.0 to 7.2, subpackaged, and then sterilized at a temperature of 121° C. for 20 min (solid medium: supplemented with 15 to 20 g of agar).

Spizizen Minimal Medium 100 mL/L of 10×Spizzen minimal salt medium, 10 mL/L of 50% (w/v) glucose, and 10 mL/L of tryptophan mother liquor (5 mg/mL), and 1.5% w/v agar were sterilized at a temperature of 121° C. for 20 min.

GM1 Medium (5 mL)

100 μL of 40% glucose, 100 μL of 20 mg/mL casein acid hydrolysate, 100 μL of 50 mg/mL yeast extract, 5 μL of 20% (w/w) MgSO$_4$.7H$_2$O, 500 μL of 10×Spizzen minimal medium, and 3195 μL of water were sterilized at a temperature of 121° C. for 20 min before being mixed.

GM2 Medium (5 mL)

100 μL of 40% glucose, 50 μL of 20 mg/mL casein acid hydrolysate, 40 μL of 20% (w/w) MgSO$_4$.7H$_2$O, 500 μL of 10×Spizzen minimal medium, and 3310 μL of water were sterilized at a temperature of 121° C. for 20 min before being mixed.

YPD Medium

1% (W/V) yeast extract, 2% peptone, and 2% glucose were diluted to 1 liter, subpackaged and then sterilized at a temperature of 115° C. for 30 min (solid medium, 1.5% w/v agar powder was added).

ΔAA Selective Medium 0.17 g of YNB (Yeast Nitrogen Base without Amino Acids), 0.5 g of $(NH_4)_2SO_4$, 2 g of glucose, 18.2 g of sorbitol, and 1.5% agar powder were added with $ddH_2O$ to 99.6 mL, and sterilized at a temperature of 115° C. for 30 min, and the medium was added with 400 μL of ΔAA before use [ΔAA formula: (1) 100 mL of ΔLeu-AA: 0.5 g of Met, 0.5 g of His and 0.5 g of Ura were added with $ddH_2O$ to 100 mL, and filtered and sterilized by a 0.22 μm filter membrane: (2) 100 mL of ΔUra-AA: 0.5 g of Met, 0.5 g of His and 0.5 g of Leu were added with $ddH_2O$ to 100 mL, and filtered and sterilized by a 0.22 μm filter membrane; (3) 100 mL of ΔLeu-AA: 0.5 g of Met, and 0.5 g of His were added with $ddH_2O$ to 100 mL, and filtered and sterilized by a 0.22 μm filter membrane.

100 mL of Liquid Medium 0.17 g of YNB, 0.5 g of $(NH_4)_2SO_4$, and 2 g of glucose were added with $ddH_2O$ to 99.6 mL, and sterilized at a temperature of 115° C. for 30 min (400 μL of ΔAA was added before use, and the ΔAA formula is the same as above).

100 mL SC-Raffinose Induction Medium 0.17 g of YNB, 0.5 g of $(NH_4)_2SO_4$, 2 g of galactose, and 1 g of raffinose were added with $ddH_2O$ to 99.6 mL, and sterilized at a temperature of 115° C. for 30 min (400 μL of ΔAA was added before use, and the ΔAA formula is the same as above).

DMEM medium: anhydrous calcium chloride. $2H_2O$ 265 mg/L, ferric nitrate. $9H_2O$ 0.10 mg/L, potassium chloride 400.0 mg/L, anhydrous magnesium sulfate 97.67 mg/L, sodium chloride 6400.0 mg/L, anhydrous sodium dihydrogen phosphate 109.0 mg/L, succinic acid 75.0 mg/L, sodium succinate 100.0 mg/L, L-arginine hydrochloride 84.0 mg/L, L-cystine hydrochloride 63.0 mg/L, glycine 30.0 mg/L, L-histidine hydrochloride 42.0 mg/L, L-isoleucine 105.0 mg/L, L-leucine 105.0 mg/L, L-lysine hydrochloride 146.0 mg/L, L-methionine 30.0 mg/L, L-phenylalanine 66.0 mg/L, L-serine 42.0 mg/L, L-threonine 95.0 mg/L, L-tryptophan 16.0 mg/L, L-tyrosine 72.0 mg/L, L-valine 94.0 mg/L, D-calcium pantothenate 4.0 mg/L, choline tartrate 7.20 mg/L, folic acid 4.0 mg/L, inositol 7.2 mg/L, nicotinamide 4.0 mg/L, riboflavin 0.40 mg/L, thiamine hydrochloride 4.0 mg/L, pyridoxine hydrochloride 4.0 mg/L, glucose 4500.0 mg/L, sodium pyruvate 110.0 mg/L, and phenol red 9.3 mg/L.

All reagents used were commercially available.

Embodiment 1 Knockout of the Gene lacZ in EC JM109 (DE3) Genome (1) Construction of Cas3 Expression Vector pCas-Cas3

Based on the DNA sequence information of the gene cas3 in *Streptomyces virginiae* IBL14/SV IBL14 genome and a vector pCas, a pair of specific primers (forward primer: pCas-cas3-F; reverse primer: pCas-cas3-R) for the gene cas3 amplification with complementary sequences to the vector pCas was designed. The SV IBL14 genomic DNA was extracted and the gene cas3 was amplified by the conventional PCR The PCR reaction system (50 μL) includes: 5 μL of 10×Pfu buffer, 5 μL of dNTPs (2.5 mM each), 1 μL of 10 μM cas3-F, 1 μL of 10 μM cas3-R, 5 μL of DMSO, 0.5 μL of Pfu DNA Polymerase, 0.5 μL of SV IBL14 genomic DNA, and 32 μL of sterile water (nuclease-free); reaction conditions: 95° C. 5 min, 94° C. 60±30 s, 55±3° C. 30 s, 72° C. 90±30 s, 2.5±0.5 U DNA polymerase (TransStart FastPfu DNA Polymerase, TransGen Biotech Co. Ltd.), 30 cycles, and 72° C. 10 min. The PCR product of full-length gene cas3 was detected by 1% agarose electrophoresis, then purified and collected by a Gel DNA Isolation Kit. The purified cas3 was ligated to a vector pKD-46 to obtain a Cas3 expression vector pCas-cas3 (FIG. 1A).

(2) Construction of Gene Editing Vector pKC1139-t/g-ΔlacZ (A) Preparation of t-ΔlacZ According to the *E. coli* JM109 (DE3)/EC JM109 (DE3) genome sequencing information, a pair of specific primers lacZ-F and lacZ-R to obtain the gene lacZ were designed and synthesized. Using the extracted EC JM109 (DE3) genomic DNA as a template, the gene lacZ was amplified by the conventional PCR method the same as step (1). The PCR product of the gene lacZ was detected by 1.5% agarose electrophoresis, then purified and collected by a DNA Isolation Kit for standby use. Both a pair of upstream homologous arm (UHA) primers lacZ-UF/UR and a pair of downstream homologous arm (DHA) primers lacZ-DF/DR of the lacZ gene which can be used for ligating the UHA and the DHA by overlap PCR were designed and synthesized according to the lacZ gene sequence. Using the purified lacZ gene as a template, the UHA and the DHA of the gene lacZ were amplified by the conventional PCR method the same as step (1). The PCR products of the UHA and the DHA were detected by 1.5% agarose electrophoresis, then purified and collected by a DNA Isolation Kit for standby use. A gene editing template t-ΔlacZ (consisting of the UHA and the DHA) was amplified by overlap PCR of 50 μL of a reaction system, and the overlap PCR reaction system includes: 5 μL of 10×Pfu buffer, 5 μL of dNTPs (2.5 mM each), 1 μL of 10 μM forward primer, 1 μL of 10 μM reverse primer, 5 μL of DMSO, 0.5 μL of Pfu DNA Polymerase, 0.5 μL+0.5 μL of upstream and downstream homologous arm DNA, and 31.5 μL of sterile water (nuclease-free); reaction conditions: 95° C. 5 min, 94° C. 60±30 s, 55±3° C. 30 s, 72° C. 90±30 s, 2.5±0.5 U DNA polymerase (1 μL of primers UF and DR were added respectively after one cycle), continued for 30 cycles, and 72° C. 10 min. The amplified product of t-ΔlacZ was detected by 1.5% agarose gel electrophoresis, then purified and collected by a DNA Isolation Kit for standby use. The synthesized t-ΔlacZ sequence table is shown in Table 2:

TABLE 2

| t-ΔlacZ Sequence | | |
|---|---|---|
| t-ΔlacZ_(as shown in SEQ ID NO: 3) | atgagcgtggtggttatgccgatcgcgtcacactacgtctgaacgtcgaaaacccg aaactgtggagcgccgaaatcccgaatctctatcgtgcggtggttgaactgcacac cgccgacggcacgctgattgaagcagaagcctgcgatgtcggtttccgcgaggtg cggattgaaaatggtctgctgctgctgaacggcaagccgttgctgattcgaggcgtt aaccgtcacgagcatcatcctctgcatggtcaggtcatggatgagcagacgatggt | 1144 bp UHA: 423 DHA: 721 |

TABLE 2-continued t-ΔlacZ Sequence

```
gcaggatatcctgctgatgaagcagaacaactttaacgccgtgcgctgttcgcatta
tccgaaccatccgctgtggtacacgctgtgcgaccgctacggcctgtatgtggtgg
atgaagccaatattgaaacccacggcatgggtttacagggcggcttcgtctgggac
tgggtggatcagtcgctgattaaatatgatgaaaacggcaacccgtggtcggctta
cggcggtgattttggcgatacgccgaacgatcgccagttctgtatgaacggtctggt
ctttgccgaccgcacgccgcatccagcgctgacggaagcaaaacaccagcagca
gttttccagttccgtttatccgggcaaaccatcgaagtgaccagcgaatacctgttc
cgtcatagcgataacgagctcctgcactggatggtggcgctggatggtaagccgc
tggcaagcggtgaagtgcctctggatgtcgctccacaaggtaaacagttgattgaa
ctgcctgaactaccgcagccggagagcgccgggcaactctggctcacagtacgc
gtagtgcaaccgaacgcgaccgcatggtcagaagccgggcacatcagcgcctg
gcagcagtggcgtctggcggaaaacctcagtgtgacgctccccgccgcgtccca
cgccatcccgcatctgaccaccagcgaaatggattttttgcatcgagctgggtaataa
gcgttggcaatttaaccgccagtcaggctttctttcacagatgtggattggcgataaa
aaacaactgctgacgccgctgcgcgatcagttcacccgtgcaccgctggataacg
acattggcgtaagtgaagcgacccgcat
```

(B) Preparation of g-ΔlacZ

A guide DNA fragment g-ΔlacZ sequentially consisting of a restriction site (BamHI), a transcription promoter, a crDNA (composed of repeat and spacer), a transcription terminator and a restriction site (EcoRI) was designed and chemically synthesized. The synthesized g-ΔLacZ sequence table is shown in Table 3, in which the uppercase represents an enzyme cutting site; the dotted line represents a complementary region; the single underline represents a promoter; the double underline represents a terminator; the italic letter represents spacer; and the bold letter represents repeat.

TABLE 3 g-ΔlacZ Sequence

| g-ΔlacZ 222 bp (as shown in SEQ ID NO: 4) | ggctgcaggtcgactctagaGGATCCtaatacgactcactatagggaatattg tcctcatcgccccttcgaggggtcgcaacccgccggtgcagtatgaaggcgg cggagccgacaccacggtcctcatcgccccttcgaggggtcgcaacataaaac gaaaggctcagtcgaaagactgggcctttcgttttatGAATTCgtaatcatgtc atagctgtt | PAM: ttc S: 40 bp R: 30 bp |
|---|---|---|

(C) Construction of pKC1139-t/g-ΔlacZ

The t-ΔlacZ and g-ΔlacZ fragments prepared according to step (2) (A) and (B) were digested and ligated to a vector pKC1139 by a T4 ligase, respectively, and transformed into E. coli DH5a to obtain a gene editing vector pKC1139-t/g-ΔlacZ (FIG. 1B);

(3) Construction and Validation of Gene-Edited Recombinant EC JM109(DE3)-ΔlacZ (A) Preparation of EC JM109 (DE3) Competent Cells An EC JM109 (DE3) monoclone was picked from a plate with a sterilized toothpick and put in 30 ml of an LB liquid medium, and cultured at a temperature of 37±5° C. and a speed of 200±100 rpm overnight; 100±50 µl of the overnight culture was transferred to 30 ml fresh LB liquid medium, and cultured at a temperature of 375° C. and a speed of 200±100 rpm for about 3±1 h until the OD600 value of a bacterial solution is 0.4 to 0.6. 1 mL of the above bacterial solution was taken to a 1.5 mL EP tube, and centrifuged at a temperature of 4° C. and a speed of 5000 rpm for 5 min. After the supernatant was removed, the competent cells of E. coli JM109 (DE3) was obtained by re-suspending the thallus precipitate with 50 µL of an SSCS solution pre-cooled on ice and stored at a temperature of −80° C. for standby use (the whole process was carried out on ice).

(B) Co-Transformation of pCas-Cas3 and pKC1139-t/g-ΔlacZ

The vectors pCas-cas3 and pKC1139-t/g-ΔlacZ were thoroughly and uniformly mixed and transformed into the EC JM109 (DE3) competent cells, and cultured overnight at a temperature of 30° C. in an LB solid medium resistant to apramycin and ampicillin coated with 5 µL of isopropyl-(β-D-thiopyran galanoside (IPTG 200 mg/mL), 40 µL of 5-bromo-4-chloro-3-indole-(β-D-galactopyranoside (X-gal20 mg/mL) and 20 µL of arabinose (10 mM/L) to obtain a transformant.

(C) PCR and DNA Sequencing of Edited Sequences in Transformant Gnomes

Figure 2:
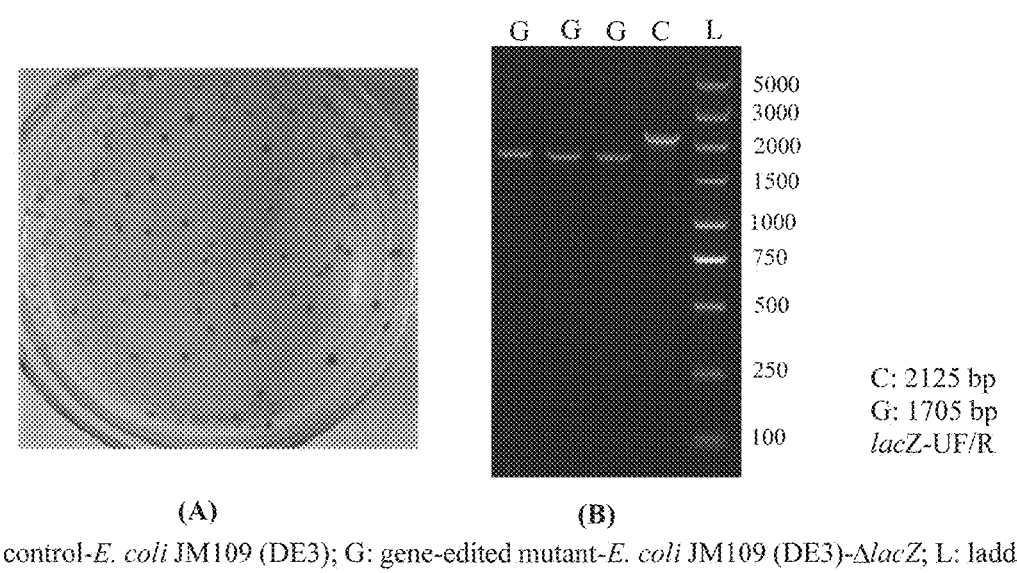
FIG. 2 shows blue-white screening and PCR validation. (A) is *E. coli* JM109(DE3) blue-white screening, the blue indicates an original strain, and the white indicates a recombinant strain; (B) is a DNA gel electrophoretogram of PCR products of the target gene lacZ, lane L: 5000 bp DNA ladder, lane C: PCR of the gene lacZ in an *E. coli* JM109 (DE3) original strain genome, lane G: PCR of the gene lacZ in a gene-edited mutant genome.
Figure 3:
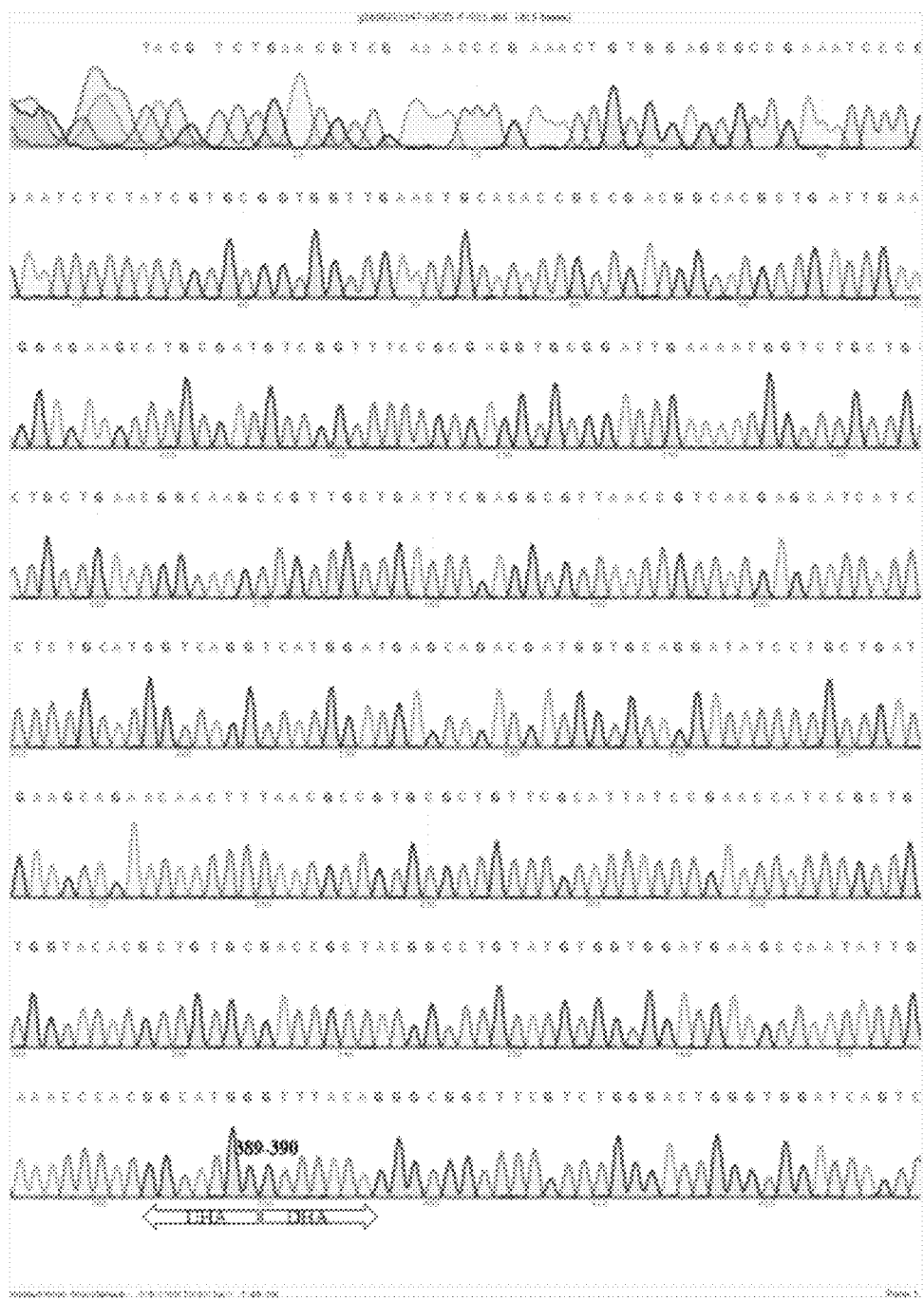
FIG. 3 shows DNA sequencing result of the gene-edited mutant *E. coli* JM109(DE3)-ΔlacZ.

White monoclones were picked and cultured (FIG. 2A). Using the extracted DNA genome of the culture as a template and lacZ-F/lacZ-R as primers, the edited sequences in transformants were amplified by the conventional PCR method same as step (1) and then detected by 1% agarose electrophoresis according to the molecular weight size of the amplified band (FIG. 2B). The sequencing (General Biosystems, Inc., Chuzhou, Anhui province, China) results show that the intersection of the UHA and the DHA is at 389 to 390 bp, which is consistent with the sequence of the gene editing fragment t-ΔlacZ, indicating that the recombinant obtained by gene editing is correct and the gene lacZ is successfully knocked out (FIG. 3).

The primers and sequences thereof involved in each step are shown in Table 4, in which the uppercase represents an enzyme cutting site; and the dotted line represents a complementary region.

TABLE 4

Primers and Sequences Thereof

| Primers | Characteristics (5' terminal to 3' terminal) |
|---|---|
| cas3-F (as shown in SEQ ID NO: 5) | <u>acttttattttaggaggcaaaagt</u>gggccgtctggacgcggtgga |
| cas3-R (as shown in SEQ ID NO: 6) | <u>aaataatcttcatctaaaatatactttt</u>cacaagacctccccggcgcggta |
| lacZ-F (as shown in SEQ ID NO: 7) | tacccaacttaatcgccttgcagcaca |
| lacZ-R (as shown in SEQ ID NO: 8) | ccgtcgatattcagccatgtgccttctt |
| pCas-cas3-F (as shown in SEQ ID NO: 9) | taccgcgccggggaggtcttgtga<u>aagtatattttagatgaagattattt</u> |
| pCas-cas3-R (as shown in SEQ ID NO: 10) | tccaccgcgtccagacggcccac<u>ttttgcctcctaaaataaaaagt</u> |
| pKC1139-lacZ-UF (as shown in SEQ ID NO: 11) | <u>gtaaaacgacggccagtgccAAGCTT</u>atgagcgtggtggttatgcc |
| pKC1139-lacZ-UR (as shown in SEQ ID NO: 12) | acgaagccgccctgtaaacccatgccgtgggtttcaata |
| pKC1139-lacZ-DF (as shown in SEQ ID NO: 13) | tattgaaacccacggcatgggtttacagggcggcttcgt |
| pKC1139-lacZ-DR (as shown in SEQ ID NO: 14) | <u>tcgcgcgcggccgcggatccCCTAGA</u>atgcgggtcgcttcacttac |

Embodiment 2 Knockout of the Gene Ldh and Insertion of a Chloramphenicol Resistant Gene Cat in BS 168

(1) Construction of Cas3 Expression Vector pHT304-Cas3

According to the DNA sequence information of the SV IBL14 gene cas3 and a vector pHT304, a pair of specific primers pHT304-cas3-F/R for the gene cas3 amplification with complementary sequences to the vector pHT304 was designed, and the remaining steps were the same as step (1) in Embodiment 1.

(2) Construction of Gene Editing Vector pKC1139-t/g-Δldh::Cat g-Δldh and t-Δldh::cat capable of expressing a chloramphenicol resistant enzyme gene cat inserted between the UHA and the DHA of the gene ldh were designed according to the ldh gene sequence in *B. subtilis*/BS 168, and the remaining steps are the same as step (2) in Embodiment 1.

The synthesized t-Δldh::cat sequence is shown in Table 5, in which the single underline represents a promoter; and the double underline represents a metabolic terminator.

TABLE 5

| | t-Δldh::cat Sequence | |
|---|---|---|
| t-Δldh::cat (as shown in SEQ ID NO: 15) | gtgatggatttaaaccacggaaaggcgtttgcgccacaaccggtcaaaacatctta cggaacatatgaagactgcaaggatgctgatattgtctgcatttgcgccggagcaa accaaaaacctggtgagacacgccttgaattagtagaaaagaacttgaagattttca aaggcatcgttagtgaagtcatggcgagcggatttgacggcattttcttagtcgcga caaatccggttgatatcctgacttacgcaacatggcgcgcctacctgtgacggaag atcacttcgcagaataaataaatcctggtgtccctgttgataccgggaagccctggg ccaacttttggcgaaaatg <u>agacgttgatcggcacgtaagaggttccaactttcaccataatgaaataagatcact accgggcgtattttttgagttgtcgagattttcaggagctaaggaagctaaaatgga</u> gaaaaaatcactggatataccaccgttgatatatcccaatggcatcgtaaagaaca ttttgaggcatttcagtcagttgctcaatgtacctataaccagaccgttcagctggata ttacggcctttttaaagaccgtaaagaaaaataagcacaagttttatccggcctttatt cacattcttgcccgcctgatgaatgctcatccggaattcgtatggcaatgaaagac ggtgagctggtgatatgggatagtgttcacccttgttacaccgttttccatgagcaaa ctgaaacgttttcatcgctctggagtgaataccacgacgatttccggcagtttctaca catatattcgcaagatgtggcgtgttacggtgaaaacctggcctatttccctaaagg gtttattgagaatatgttttctgctcagccaatccctgggtgagtttcaccagtttgat ttaaacgtggccaatatggacaacttcttcgcccccgttttcaccatgggcaaatatt atacgcaaggcgacaaggtgctgatgccgctggcgattcaggttcatcatgccgtc tgtgatggcttccatgtcggcagaatgcttaatgaattacaacagtactgcgatgagt ggcagggcggggcgtaa<u>ggcgcgccatttaaatgaagttcctattccgaagttcc</u> cgatgcgtacaaacaagaggagctggaccaaattgtagatgatgtgaaaaacgca | 1397 bp UHA: 358 Cat: 807 DHA: 232 |

TABLE 5-continued t-Δldh::cat Sequence

```
gcttaccatatcattgagaaaaaaggcgcgacttattatggggttgcgatgagtcttg
ctcgcattacaaaagccattcttcataatgaaaacagcatattaactgtcagcacatat
ttggacgggcaatacggtgcagatgacgtgtacatcggtgtgccggctgtcgtgaa
tcgc
```

The synthesized g-Δldh sequence is shown in Table 6, in which the uppercase represents an enzyme cutting site; the single underline represents a promoter; the double underline represents a metabolic terminator; the italic letter represents spacer; and the bold letter represents repeat.

TABLE 6 g-Δldh Sequence

| | | |
|---|---|---|
| g-Δldh<br>291 bp<br>(as shown<br>in SEQ<br>ID NO: 16) | ggctgcaggtcgactctagaGGATCCtaatgtgagttagctcactcattaggcacccca<br>ggctttacactttatgcttccggctcgtatgttgtgtggaattgtgagcggataacaagtcctc<br>*atcgcccttcgaggggtcgcaac*agcggcctgccaaaagagcgggtgattggaagc<br>ggcacaagtcctcatcgcccttcgaggggtcgcaacctagcataaccccttggggcct<br>ctaaacgggtcttgagggttttttgGAATTCgtaatcatgtcatagctgtt | PAM: ttc<br>S: 40 nt<br>R: 30 nt |

(3) Construction and Validation of Gene-Edited Recombinant BS 168-Δldh::Cat (A) Preparation of BS 168 Competent Cells BS 168 monoclones were picked and cultured in 5 mL of a GM1 medium overnight at a temperature of 37° C. and a speed of 130 rpm. The next day, 1 mL of the overnight culture solution was transferred to 9 mL of fresh GM1 medium and cultured at a temperature of 37° C. and a speed of 200 rpm for 3.5 h. 5 mL of the GM1 culture was transferred to 45 mL of fresh GM2 medium and then cultivated at a temperature 37° C. and a speed of 130 rpm for 1.5 h. Centrifuging was carried out at a speed of 4000 rpm for 10 min. An appropriate amount of supernatant was reserved for re-suspending the cells, and the BS 168 competent cells were subpackaged into a 2 mL EP tube for standby use.

(B) Co-Transformation of pHT304-Cas3 and pKC1139-t/g-Δldh::Cat

The vectors pHT304-cas3 and pKC1139-t/g-Δldh::cat were gently mixed well and then added to the BS 168 competent cells, allowed to stand at a temperature of 37° C. for 1 h, and cultured at a speed of 220 rpm for 3 to 4 h. A suitable amount of a bacterial solution was sucked and coated onto an LB plate containing chloramphenicol/Cm, and cultured in a 37° C. incubator.

(C) PCR and DNA Sequencing of Edited Sequences in Transformant Gnomes

Monoclones were picked on the LB plate containing Cm and cultured overnight at a temperature of 37° C. and a speed of 200 rpm. The next day, the genome of the cultured transformant cells was extracted and the PCR products of the edited sequences in the genome were detected by 1% agarose electrophoresis. The change in the band size of the PCR products of the edited sequences was observed, and it was proved that in BS 168, the ldh gene knockout and the cat gene insertion were successful by DNA sequencing.

The primers and sequences thereof involved in each step are shown in Table 7, in which the uppercase represents enzyme cutting sites; and the dotted line represents a complementary region.

TABLE 7

Primers and Sequences Thereof

| Primers | Characteristics (5' terminal to 3' terminal) |
|---|---|
| cas3-F | acttttattttaggaggcaaaagtgggccgtctggacgcggtgga |
| cas3-R | aaataatcttcatctaaaatatactttcacaagacctccccggcgcggta |
| ldh-F (as shown in SEQ ID NO: 17) | atgatgaacaaacatgtaa |
| ldh-R (as shown in SEQ ID NO: 18) | ttagttgacttttttgttc |
| pHT304-cas3-F (as shown in SEQ ID NO: 19) | taacaatttcacacaggaAACAGCtgtggtcgccggtgccccgaac |
| pHT304-cas3-R (as shown in SEQ ID NO: 20) | ttggcgggtgtcgggggctggcttaatcacaagacctccccggcgc |

TABLE 7-continued

Primers and Sequences Thereof

| Primers | Characteristics (5' terminal to 3' terminal) |
|---|---|
| pKC1139-ldh-UF (as shown in SEQ ID NO: 21) | gtaaaacgacggccagtgccAAGCTTcgatgagatggatttaaacca |
| pKC1139-ldh-UR (as shown in SEQ ID NO: 22) | tttttctcaacgagttcactatgttgcgtaagtcaggata |
| pKC1139-ldh-CmF (as shown in SEQ ID NO: 23) | tatcctgacttacgcaacatggcgcgcctacctgtg |
| pKC1139-ldh-CmR (as shown in SEQ ID NO: 24) | cacaggtaggcgcgccatgttgcgtaagtcaggata |
| pKC1139-ldh-DF (as shown in SEQ ID NO: 25) | tatcctgacttacgcaacatagtgaactcgttgagaaaaa |
| pKC1139-ldh-DR (as shown in SEQ ID NO: 26) | tcgcgcgcggccgcggatccTCTAGAgcgattcacgacagcc |

Embodiment 3 Double Plasmid Knockout of the crtE Gene in SC BY4741

(1) Construction of Cas3 Expression Vector pRS415-Cas3

Except that a pair of specific primers pRS415-cas3-F/R for the base-optimized cas3 gene amplification with complementary sequences to the vector pRS415, a gall promoter in the upstream of the gene cas3 and a nuclear localization signal plus a CYC1 terminator in the downstream of the gene cas3 were designed according to the DNA sequence information of the vector pRS415, the remaining steps are the same as step (1) in Embodiment 1.

(2) Construction of Gene Editing Vector pYES2-NTA-t/g-ΔcrtE

Except that g-ΔcrtE was designed and t-ΔcrtE was designed and synthesized according to the crtE gene sequence in Saccharomyces cerevisiae/SC BY4741, the remaining steps are the same as step (2) in Embodiment 1.

The synthesized t-ΔcrtE sequence is shown in Table 8.

TABLE 8 t-ΔcrtE Sequence

| t-ΔcrtE (as shown in SEQ ID NO: 27) | cagccattccattggagtttactccacaagatgatattgttttgttggaaccatatc<br>attatttgggaaaaaatcctggtaaagaaattcgttcacaattgattgaagcctttta<br>attattggttggatgttaaaaaagaggaccttgaagttattcaaaatgttgttggta<br>tgttgcatactgcttctttgctcatggatgatgttgaagatagttccgttttacgtcg<br>gggttcaccagttgctcatttgatctacggtattccacaaactattaatacagcca<br>attatgtttactttttagcctatcaagaaatttttaaattgcgtccaacacctattcct<br>atgccagttggtggttttgtttcgtattgccgttcgtttgatgatggccaaatctgaa<br>tgtgatattgattttgttcaattagttaatttgattagtatctattttcaaattcgtgatg<br>attatatgaatcttcaatctagtgaatatgcacataacaaaaattttgccgaggac<br>cttactgaaggtaaattttccttttccaactattcatagtattcatactaatccaagta<br>gtcgtttagttattaatacattacagaaaaaatctacatccccagaaattttgcatc<br>attgtgttaattatatgcgtactgaaacacattcctttgaatatactcgtgaagtttt<br>gaatactttgtccggtgccttggaacgtgaattgggtcgtttgcaagaagaattt<br>gccgaagctaatagtcgtatggatttgggcgacgttgaatccgaaggtcgtac<br>agggaaaa | 807 bp<br>UHA: 353<br>DHA: 454 |

The synthesized g-ΔcrtE sequence is shown in Table 9, in which the uppercase represents an enzyme cutting site; the single underline represents a promoter; the double underline represents a metabolic terminator; the italic letter represents spacer; and the bold letter represents repeat.

TABLE 9 g-ΔcrtE Sequence

| g-ΔcrtE (as shown in SEQ ID NO: 28) | cgGAATTCtctttgaaaagataatgtatgattatgctttcactcatatttatacagaa<br>acttgatgttttctttcgagtatatacaaggtgattacatgtacgtttgaagtacaactcta<br>gattttgtagtgccctcttgggctagcggtaaaggtgcgcatttttttcacaccctacaat<br>gttctgttcaaaagatttttggtcaaacgctgtagaagtgaaagttggtgcgcatgtttcg<br>gcgttcgaaacttctccgcagtgaaagataaatgatcgtcctcatcgccccttcgag<br>gggtcgcaac*tagtgcctcatcttcttcttcagcatcctccgaaaatggt*gtcctcat<br>cgccccttcgaggggtcgcaactttttttgtttttatgtct*CTCGAGcgg | PAM: ttc<br>S: 40 nt<br>R: 30 nt |

(3) Construction and Validation of Gene-Edited Recombinant SC BY4741-ΔcrtE (A) Preparation of SC BY4741 Competent Cells SC BY4741 monoclones were picked from a plate with a sterilized toothpick and cultured in 50 ml of a YPD liquid medium at a temperature of 30° C. and a speed of 200 rpm until OD600 was 1.3 to 1.5, placed on ice for 10 min, and then centrifuged at a speed of 8000 rpm for 5 min, and the precipitate was added with 25 mL of ddH₂O, and centrifuged and washed at a speed of 5000 rpm for 5 min; the precipitate was added with 25 mL of sorbitol (1M) again and centrifuged and washed at a speed of 5000 rpm for 5 min, the precipitate after washing was first added with 2 mL of an LiAc/DTT/TE buffer solution to suspend, and then added with 25 mL of the buffer solution, sealed with a sealing membrane, and cultured at a temperature of 30° C. for 30 min, and then the thallus was collected by centrifuging at a speed of 5000 rpm for 5 min; the thallus was suspended in 1 mL of ddH₂O and transferred to a 1.5 mL EP tube, and centrifuged at a speed of 4000 rpm for 3 min; the precipitate was suspended in 1 mL of iced sorbitol, and centrifuged and washed at a speed of 4000 rpm for 3 min, and the washed cell was added with 100 to 200 μL of sorbitol to be suspended and subpackaged to obtain competent cells, which was stored at a temperature of −80 degrees for standby use (the whole operation was carried out at a temperature 4° C.).

(B) Obtaining of SC BY4741-ΔcrtE Transformant

100 μL of the competent cells was added with 3 to 10 μL of pRS415-cas3, transferred to an electroporation cuvette (2 mM), uniformly mixed and then allowed to stand for 5 min on ice, and immediately added with 900 μL of iced sorbitol after electric shock (1.5 kV, 5 mS) to be uniformly mixed, then 1 to 100 μL was took to coat a plate (a medium ΔLeu-ΔA: Met, His, and Ura was selected), the culturing was carried out at a temperature of 30° C. for 3 days, and a PCR-validated transformant SC BY4741-pRS415-cas3 grown on a selective plate was stored in a plate or glycerol tube. The obtained SC BY4741-pRS415-cas3 transformant was cultivated for the protein Cas3 expression by an SC-raffinose induction (induced at a temperature of 25° C. and a speed of 200 rpm for 1 day, and then induced at a temperature of 30° C. and a speed of 200 rpm for 1 day), and the induced strain was used for preparing the competent cells according to Embodiment 3 (3) (A); the obtained SC BY4741-pRS415-cas3 competent cells was transformed with a pYES2-t/g-crtE plasmid according to the above method for preparing the transformant SC BY4741-pRS415-cas3 to obtain a potential SC BY4741-ΔcrtE transformant.

(C) PCR and DNA Sequencing of Edited Sequences in Transformant Gnomes

Monoclones of the potential SC BY4741-ΔcrtE transformant were picked and put in a YPD liquid medium and cultured at a temperature of 30° C. and a speed of 200 rpm for 1 to 2 days, the genomic DNA of the culture was extracted, and a PCR amplification for the gene crtE was carried by using the extracted genomic DNA as a template and crtE-F/crtE-R as verification perimers. It was proved that the crtE gene knockout was successful by the electrophoresis and sequencing method of Embodiment 1 (1).

The primers and sequences thereof involved in each step are shown in Table 10, in which the uppercase represents an enzyme cutting site; and the dotted line represents a complementary region.

TABLE 10

Primers and Sequences Thereof

| Primers | Characteristics (5' terminal to 3' terminal) |
| --- | --- |
| cas3-F | acttttattttaggaggcaaaagtgggccgtctggacgcggtgga |
| cas3-R | aaataatcttcatctaaaatatactttcacaagacctccccggcgcggta |
| crtE-F (as shown in SEQ ID NO: 29) | cagcatacacctcactagggtag |
| crtE-R (as shown in SEQ ID NO: 30) | ccccttccagtgcatatgcaa |
| pYES2-crtE-UF (as shown in SEQ ID NO: 31) | cccAAGCTTcagccattccattggagtttactcc |
| p-YES2-crtE-UR (as shown in SEQ ID NO: 32) | aacggcaatacgaaacaaaccaccaactggcataggaataggtgttggac |
| pYES2-crtE-DF (as shown in SEQ ID NO: 33) | gtccaacacctattcctatgccagttggtggtttgtttcgtattgccgtt |
| pYES2-crtE-DR (as shown in SEQ ID NO: 34) | cgcGGATCCttttccctgtacgaccttcggatt |
| pRS415-F+ (as shown in SEQ ID NO: 35) | tatagggccggtgaagttttaagcagggctgacccaag |
| pRS415-R (as shown in SEQ ID NO: 36) | caacggcatccaatctacccattttttccggggggatccactagttc |

TABLE 10-continued

Primers and Sequences Thereof

| Primers | Characteristics (5' terminal to 3' terminal) |
|---|---|
| pRS415-cas3-F (as shown in SEQ ID NO: 37) | aaaaaaatgggtagattggatgccgttg |
| pRS415-cas3-R (as shown in SEQ ID NO: 38) | gtcagccctgcttaaaacttcaccggccctatatgcag |

Embodiment 4 Single Plasmid Knockout of the crtE Gene in SC BY4741

(1) Construction of Cas3 Expression Vector pRS415-cas3
The step is the same as step (1) in Embodiment 3.
(2) Construction of Gene Editing Fragment t-ΔcrtE
The step is the same as the construction of t-ΔcrtE in step (2) in Embodiment 3.
(3) Construction and Validation of Gene-Edited Recombinant SC BY4741-ΔcrtE
(A) Preparation of SC BY4741 Competent Cells
The step is the same as step (3) (A) in Embodiment 3.
(B) Obtaining of SC BY4741-ΔcrtE Transformant
Except that a t-ΔcrtE fragment and pRS415-cas3 were simultaneously transformed into the SC BY4741 competent cells, the remaining steps were the same as step (3) (B) in Embodiment 3.
(C) PCR and DNA Sequencing of Edited Sequences in Transformant Gnomes
The step is the same as step (3) (C) in Embodiment 3.

Embodiment 5 Knockout of the Drosha Gene and Insertion of Hygromycin B Resistant Gene Hyg in HEK293

1. (1) Construction of Cas3 Expression Vector pCAS9-BFP-Cas3
Except that the base-optimized cas3 gene instead of the cas3 gene in SV IBL14 genome and pCAS9-BFP instead of pRS415-cas3 as described in step (1) in Embodiment 3 were used, the remaining steps are the same as step (1) in Embodiment 1.
(2) Gene Editing Vector pUC19-t/g-Δdrosha::hyg
Except that g-Δdrosha and t-Δdrosha::hyg capable of expressing hygromycin B resistant gene hyg R (derived from a plasmid pSilencer2.1-U6hygro) inserted between the UHA and the DHA of the drosha gene were designed according to the drosha gene sequence of HEK293 and pUC19 vector sequence, the remaining steps are the same as step (2) in Embodiment 1.
The synthesized t-Δdroshay::hyg sequence is shown in Table 11.

TABLE 11

| t-Δdroshay::hyg Sequence | | |
|---|---|---|
| t-Δdrosha::hyg (as shown in SEQ ID NO: 39) | tggcttgactaggggtctttgagttgctcatcaagatggtcaggcatttatgaaacc<br>ctgtttacatagtaagaattattttttaaaaaaacttttcccttttttcttttctgccatgaagt<br>cacagaatgtcgttccaccgggacgagggtgtccccgaggacgaggaggacat<br>ggagccagaccctcagcaccatcctttaggccccaaaatctgaggctgcttcaccc<br>tcagcagcctcctgtgcaatatcaatatgaacctccaataagatacattgatgagttt<br>ggacaaaccacaactagaatgcagtgaaaaaaatgctttatttgtgaaatttgtgatg<br>ctattgctttatttgtaaccattataagctgcaataaacaagttggggtgggcgaaga<br>actccagcatgagatccccgcgctggaggatcatccagccggcgtcccggaaaa<br>cgattccgaagcccaacctttcatagaaggcggcggtggaatcgaaatctcgtagc<br>acgtgctattcctttgccctcggacgagtgctggggcgtcggttttccactatcggcg<br>agtacttctacacagccatcggtccagacggccgcgcttctgcgggcgatttgtgta<br>cgcccgacagtcccggctccggatcggacgattgcgtcgcatcgaccctgcgcc<br>caagctgcatcatcgaaattgccgtcaaccaagctctgatagagttggtcaagacc<br>aatgcggagcatatacgcccggagccgcggcgatcctgcaagctccggatgcct<br>ccgctcgaagtagcgcgtctgctgctccatacaagccaaccacggcctccagaag<br>aagatgttggcgacctcgtattgggaatccccgaacatcgcctcgctccagtcaat<br>gaccgctgttatgcggccattgtccgtcaggacattgttggagccgaaatccgcgt<br>gcacgaggtgccggacttcggggcagtcctcggcccaaagcatcagctcatcga<br>gagcctgcgcgacggacgcactgacggtgtcgtccatcacagtttgccagtgata<br>cacatggggatcagcaatcgcgcatatgaaatcacgccatgtagtgtattgaccga<br>ttccttgcggtccgaatgggccgaacccgctcgtctggctaagatcggccgcagc<br>gatcgcatccatggcctccgcgaccggctgcagaacagcgggcagttcggtttca<br>ggcaggtcttgcaacgtgacaccctgtgcacggcgggagatgcaataggtcagg<br>ctctcgctgaattccccaatgtcaagcacttccggaatcgggagcgcggccgatgc<br>aaagtgccgataaacataacgatctttgtagaaaccatcggcgcagctatttacccg<br>caggacatatccacgccctcctacatcgaagctgaaagcacgagattcttcgccct<br>ccgagagctgcatcaggtcggagacgctgtcgaacttttcgatcagaaacttctcg<br>acagacgtcgcggtgagttcaggctttttcatcacgtgctgatcagatccgaaaatg<br>gatatacaagctcccgggagcttttttgcaaaagcctaggcctccaaaaaagcctcc<br>ccactacttctggaatagctcagaggcagaggcggcctcggcctctgcataaataa<br>aaaaaattagtcagccatggggcggagaatgggcggaactgggcggagtttagg<br>ggcgggatgggcggagttaggggcgggactatggttgctgactaattgagatgca<br>cagactttgtacccttcccccaccccatgcctccgtcagcgcaaggccctcttcccc | 1972 bp<br>UHA: 270<br>Hrg-1522<br>DHA: 180 |

TABLE 11-continued t-Δdroshay::hyg Sequence cctgcccaatcaggccgcctttccccaaccaccagatgaggcacccttcccagtt
cctccttgttttcctcccatgccaccaccaatgccttgtcctaataacccccagtccc
tggggcac The synthesized g-Δdrosha sequence is shown in Table 12, in which the single underline represents a promoter; the double underline represents a metabolic terminator; the italic letter represents spacer; and the bold letter represents repeat.

TABLE 12 g-Δgrosha Sequence

| g-Δdrosha 166 bp (as shown in SEQ ID NO: 40) | Taatacgactcactataggg<u></u>aatattgtcctcatcgcccttcgagggg tcgcaaccaccactttctcaaactctccagcccccaattttctgtcctcatcgcccttcgaggggtcgcaacataaaacgaaaggctcagtcgaaa gactgggcctttcgttttat | PAM: ttc S: 36 nt R: 30 nt |

(3) Construction and Validation of Gene-Edited Recombinant HEK293-Δdrosha::hyg

HEK293 cells were inoculated in a 6-well plate containing a DMEM medium and cultured at a temperature of 37° C. When the cell confluence rate reached 80%, the constructed vectors pCAS9-BFP-cas3 (1 μg) and pUC19-t/g-Δdrosha::hyg (1.5 μg) co-transfect the HEK293 cells (Lipofectamine 2000 transfection reagent), a fresh cell culture solution was replaced after 6 hours, and the transfected HEK293 cell was inoculated into a large cell culture dish after 5 days (1×10⁶ cells/dish), hygromycin B (300 μg/mL) was added after 1 day, then a fresh hygromycin B-containing medium was replaced every 2 to 3 days, and about 10-15 days after the hygromycin B was added, macroscopic monoclones appearing in the cell culture dish were inoculated and passed to another 6-well plate. When the cells were cultured and overgrown on a resistant plate, the genome was extracted for PCR, and the PCR product was detected by 1% agarose electrophoresis, the change in size of the band size of the PCR products of the edited sequences was observed, and it was proved that in HEK293 cells the drosha gene knockout and hygromycin B resistant gene insertion were successful by DNA sequencing.

The primers and sequences thereof involved in each step are shown in Table 13, in which the dotted line represents a complementary region.

TABLE 13

Primers and Sequences Thereof

| Primers | Characteristics (5' terminal to 3' terminal) |
|---|---|
| cas3-F | acttttattttaggaggcaaaagtgggccgtctggacgcggtgga |
| cas3-R | aaataatcttcatctaaaatatactttcacaagacctccccggcgcggta |
| drosha-F (as shown in SEQ ID NO: 41) | accgcgcacaaggccc |
| drosha-R (as shown in SEQ ID NO: 42) | taagacagatgactgacattccacctaattaatatccca |
| drosha-UF (as shown in SEQ ID NO: 43) | tgcactccagcttagggacagagt |
| drosha-UR (as shown in SEQ ID NO: 44) | caattaccataacactaattttgtagtttccaatacacttagcct |
| drosha-DF (as shown in SEQ ID NO: 45) | tggagcagctttaaggaatggtcgg |
| drosha-DR (as shown in SEQ ID NO: 46) | ctcgctcccgccgatcc |
| pUC19-drosha-UF (as shown in SEQ ID NO: 47) | acacaggaaacagcttgcactccagcttagggacag |
| pUC19-drosha-UR (as shown in SEQ ID NO: 48) | tttttcatcaattaccataacactaattttgtagtttccaatacac |

TABLE 13-continued

Primers and Sequences Thereof

| Primers | Characteristics (5' terminal to 3' terminal) |
|---|---|
| pUC19-drosha-hygF (as shown in SEQ ID NO: 49) | gtaattgatgaaaaagcctgaactcaccgc |
| pUC19-drosha-hygR (as shown in SEQ ID NO: 50) | ctgctccactattcctttgccctcggacg |
| pUC19-drosha-UF (as shown in SEQ ID NO: 51) | ggaatagtggagccagctttaaggaatggtcg |
| pUC19-drosha-UR (as shown in SEQ ID NO: 52) | tcggggctggcttaactcgctcccgccgat |
| pCAS9-BFP-cas3-F (as shown in SEQ ID NO: 53) | gccgccgcgatcgccgtgggccgtaggac |
| pCAS9-BFP-cas3-R (as shown in SEQ ID NO: 54) | gcgttttacagggtcacaagacacccgg |

The technical content of the present invention is further described by way of embodiments only above, so that a reader can understand the present invention more easily, but the embodiments of the present invention are not limited thereto, and any technology extension or recreation made according to the present invention are all protected by the present invention.

What is claimed is:

1. A type I-B CRISPR-Cas system cas3 gene-based gene editing method comprising the following step:
performing a gene editing on genetic materials of all organisms by using a gene editing tool consisting of a protein Cas3 expression vector comprising the cas3 gene of *Streptomyces virginiae* IBL14 as set forth in SEQ ID NO: 1, and a gene editing vector comprising a t-DNA and/or a g-DNA.

2. The type I-B CRISPR-Cas system cas3 gene-based gene editing method according to claim 1, further comprising the following steps:
(1) construction of Cas3 expression vector designing primers based on a sequence information of the cas3 gene using a *Streptomyces virginiae* IBL14 genome as a template, amplifying to obtain the cas3 gene by a PCR reaction, and ligating the cas3 gene to a vector to obtain the Cas3 expression vector;
(2) construction of gene editing vector
(A) designing primers according to a sequence of a gene of interest, using a biological genome of the interest as a template, designing and synthesizing a t-DNA fragment with a desired genetic function by PCR, wherein the t-DNA fragment has upstream and downstream homologous arms of the gene of interest;
(B) designing and chemically synthesizing a g-DNA fragment sequentially consisting of a restriction site, a transcription promoter, a crDNA for transcribing a crRNA, a transcription terminator, and a restriction site according to a sequence information of a biological target gene; and
(C) respectively ligating the t-DNA fragment and the g-DNA fragment to a vector to obtain the gene editing vector;
(3) construction and validation of gene-edited recombinant preparing competent cells or protoplasts, and introducing the Cas3 expression vector obtained in the step (1) and the gene editing vector obtained in the step (2) into the competent cells or the protoplasts to obtain the gene-edited recombinant; performing PCR and DNA sequencing and/or functional analysis on a recombinant chromosomal gene to confirm the gene-edited recombinant.

3. The type I-B CRISPR-Cas system cas3 gene-based gene editing method according to claim 1, wherein the t-DNA is a chemically or biologically synthesized t-DNA fragment with a desired genetic function, and the chemically or biologically synthesized t-DNA fragment is combined with the Cas3 expression vector or the gene editing vector, or exists independently.

4. The type I-B CRISPR-Cas system cas3 gene-based gene editing method according to claim 1, wherein the g-DNA is a chemically or biologically synthesized g-DNA fragment configured to transcribe the g-DNA into a crRNA, and the chemically or biologically synthesized g-DNA fragment binds into the Cas3 expression vector or the gene editing vector.

5. The type I-B CRISPR-Cas system cas3 gene-based gene editing method according to claim 1, wherein the genetic materials of all organisms are genetic materials originated from prokaryotic cells, or eukaryotic cells, and/or viruses without cellular structures.

6. The type I-B CRISPR-Cas system cas3 gene-based gene editing method according to claim 1, wherein the gene editing is a genome editing mediated through specific cleavage of Cas3 on a target DNA guided by a crRNA or the t-DNA.

7. The type I-B CRISPR-Cas system cas3 gene-based gene editing method according to claim 1, wherein the gene editing is one selected from the group consisting of deletion, insertion, scarless point mutation, and a combination of the deletion, insertion, scarless point mutation performed on biological genetic materials.

8. The type I-B CRISPR-Cas system cas3 gene-based gene editing method according to claim 2, wherein the t-DNA is a chemically or biologically synthesized t-DNA fragment with the desired genetic function, and the chemically or biologically synthesized t-DNA fragment is combined with the Cas3 expression vector or the gene editing vector, or exists independently.

9. The type I-B CRISPR-Cas system cas3 gene-based gene editing method according to claim 2, wherein the g-DNA is a chemically or biologically synthesized g-DNA fragment configured to transcribe to obtain the crRNA, and the chemically or biologically synthesized g-DNA fragment binds into the Cas3 expression vector or the gene editing vector.

* * * * *

SEQUENCE LISTING

<160> NUMBER OF SEQ ID NOS: 54

<210> SEQ ID NO 1
<211> LENGTH: 2316
<212> TYPE: DNA
<213> ORGANISM: Streptomyces virginiae IBL14

<400> SEQUENCE: 1

```
gtgggccgtc tggacgcggt ggaggacgtc ttcggcggca ggttctggcc cgtcgtggaa      60
ctcgctggcc tcacccacga cgccggcaag attcccgaag gcttccagcg gatgctggcg     120
ggatacagcc gtgcctgggg tgagcgtcac gaagtcgcct cgttgggctt cctgcccgcg     180
ctcatcggcg acccggacgt gctgttgtgg gtggcgaccg cggtcgccac ccaccatcgt     240
ccgctgaccg gccagaacgg acgcgacctg cagactctct acagcggtgt caccatcacc     300
gagctcgcgc accgtttcgg gccttttgac ccacgcgctg tccccgcctt ggaggcctgg     360
cttcgtgcga gcgccatccg ggtcggcctc ccgcggccg ctgttccaga cgacggcacg     420
ctcaccgaca ccggagtggt cgctggcgcc caccagctgc tggaggagat tttggaccgt     480
tgggcagacc gtgtgaggcc tgaggtgggc ttggccgctg tactgctgca ggggcggtc     540 accctggccg accacttgtc ctccgcccat caggctctgc ccaccgtcca gccgttgggg     600
gccgggttcc ggtcccggtt ggagaaggag ttcgctgaac gcggcaggac cctgcgtgcc     660
caccagctgg aggccgccac cgttaccgga catcttctgc tgcgcgggcc gaccggcagt     720
gggaagaccg aggctgccct gctgtgggct gccagccagg tcgaggccct gaaggcggaa     780
```

| | |
|---|---|
| ggccggggcg tgccgcgtgt gtttttcact ctcccctacc tggcctccat caacgccatg | 840 |
| gcaacacggc tgggtgacac tctcggcgat ggtgaggctg tcggcgttgc ccactcccgc | 900 |
| gccgcctcct accaccttgc ccaggccatc gccccgcagg acggcgacga ggaggacgaa | 960 |
| cacggagccc cctgccgtgt tgacgcggcc gccaaggcct tgtcccgggc cgctgccacc | 1020 |
| aagctgttcc gcgagagtgt ccgcgtcgcc acccctacc agcttctgcg gccgccctg | 1080 |
| gccgggccgg cccactccgg catcctcatc gacgccgcga actcggtgtt catcctggac | 1140 |
| gaactccacg cctacgacgc ccgcaggctc ggctacatcc tggccagtgc ccggctgtgg | 1200 |
| gaacgcctcg gtggacggat cacagtcctg tccgcgaccc tgcccagggc cctggccgac | 1260 |
| ctgttcgaga gcaccctcac cgcccccatc accttcctcg cacccccga cctcgggctg | 1320 |
| ccggcgcgcc acctcctgca cacccgaggc caccatctca ccgacccggc cacactggag | 1380 |
| gagatccgtc tgcggctgtc ccgggacgag tcggtcctgg tgatcgccaa caacgtgtcc | 1440 |
| caggccatcg ccctgtacga acagctcgca cccgacgtgt gtgaacgctt cggtcaggac | 1500 |
| gccgcgctac tgctgcactc ccggtttcga cggatggacc ggtcccggat tgagcagaag | 1560 |
| atcgccgacc ggttcgccac tgtggcacct gatgcccaga acagccgtaa gccgggcctg | 1620 |
| gtcgttgcca cgcaggtggt cgaggtcagt ctcgacgtcg acttcgatgt gctgttcact | 1680 |
| ggagcggctc cgctcgaggc cctcctgcag cgcttcggcc ggaccaaccg cgtcggggcc | 1740 |
| cgcccgccgg ccgacgtcat cgtccaccat cccgcctgga ccacacgccg ccgacagccc | 1800 |
| ggcgagtacg ccgacggcat ctacccacgg gagccggtcg agtccgcgtg cacatcctc | 1860 |
| acccgcaatc acgggcgagt catcgacgaa gcggacgcca ccgcgtggct ggacgaggtc | 1920 |
| tacgccacgg actggggcag gcaatggcac cgcgaggtgc tggagcggcg agaaagattc | 1980 |
| gaccgtgcgt tcctgcagtt ccgctacccc ttcgaagacc gcactgacct ggccgatacc | 2040 |
| ttcgacgaac tcttcgacgg ctccgaagcc atcctcgccg aagaccagga cgcctactca | 2100 |
| gccgcactgg ccgcaccaga cggcgaccac cccggagctg gccggctcct cgcagaggaa | 2160 |
| tacctcatcc ccgttcccca ctgggccagc cccctcagcc gctacgagaa gcagctcaaa | 2220 |
| gtccgcgtca tcaacggcga ctaccacccc gaccacggcc tcatggcggt ccgggggctg | 2280 |
| ccccagcccg cctaccgcgc cggggaggtc ttgtga | 2316 |

<210> SEQ ID NO 2
<211> LENGTH: 771
<212> TYPE: PRT
<213> ORGANISM: Streptomyces virginiae IBL14

<400> SEQUENCE: 2

```
Val Gly Arg Leu Asp Ala Val Glu Asp Val Phe Gly Gly Arg Phe Trp
1               5                   10                  15

Pro Val Val Glu Leu Ala Gly Leu Thr His Asp Ala Gly Lys Ile Pro
            20                  25                  30

Glu Gly Phe Gln Arg Met Leu Ala Gly Tyr Ser Arg Ala Trp Gly Glu
        35                  40                  45

Arg His Glu Val Ala Ser Leu Gly Phe Leu Pro Ala Leu Ile Gly Asp
    50                  55                  60

Pro Asp Val Leu Leu Trp Val Ala Thr Ala Val Ala Thr His His Arg
65                  70                  75                  80

Pro Leu Thr Gly Gln Asn Gly Arg Asp Leu Gln Thr Leu Tyr Ser Gly
                85                  90                  95

Val Thr Ile Thr Glu Leu Ala His Arg Phe Gly Pro Phe Asp Pro Arg
```

-continued

```
                100                 105                 110
Ala Val Pro Ala Leu Glu Ala Trp Leu Arg Ala Ser Ala Ile Arg Val
            115                 120                 125
Gly Leu Pro Ala Ala Ala Val Pro Asp Asp Gly Thr Leu Thr Asp Thr
            130                 135                 140
Gly Val Val Ala Gly Ala His Gln Leu Leu Glu Glu Ile Leu Asp Arg
145                 150                 155                 160
Trp Ala Asp Arg Val Arg Pro Glu Val Gly Leu Ala Ala Val Leu Leu
                165                 170                 175
Gln Gly Ala Val Thr Leu Ala Asp His Leu Ser Ser Ala His Gln Ala
            180                 185                 190
Leu Pro Thr Val Gln Pro Leu Gly Ala Gly Phe Arg Ser Arg Leu Glu
            195                 200                 205
Lys Glu Phe Ala Glu Arg Gly Arg Thr Leu Arg Ala His Gln Leu Glu
            210                 215                 220
Ala Ala Thr Val Thr Gly His Leu Leu Leu Arg Gly Pro Thr Gly Ser
225                 230                 235                 240
Gly Lys Thr Glu Ala Ala Leu Leu Trp Ala Ala Ser Gln Val Glu Ala
                245                 250                 255
Leu Lys Ala Glu Gly Arg Gly Val Pro Arg Val Phe Phe Thr Leu Pro
            260                 265                 270
Tyr Leu Ala Ser Ile Asn Ala Met Ala Thr Arg Leu Gly Asp Thr Leu
            275                 280                 285
Gly Asp Gly Glu Ala Val Gly Val Ala His Ser Arg Ala Ala Ser Tyr
            290                 295                 300
His Leu Ala Gln Ala Ile Ala Pro Gln Asp Gly Asp Glu Glu Asp Glu
305                 310                 315                 320
His Gly Ala Pro Cys Arg Val Asp Ala Ala Lys Ala Leu Ser Arg
                325                 330                 335
Ala Ala Ala Thr Lys Leu Phe Arg Glu Ser Val Arg Val Ala Thr Pro
            340                 345                 350
Tyr Gln Leu Leu Arg Ala Ala Leu Ala Gly Pro Ala His Ser Gly Ile
            355                 360                 365
Leu Ile Asp Ala Ala Asn Ser Val Phe Ile Leu Asp Glu Leu His Ala
            370                 375                 380
Tyr Asp Ala Arg Arg Leu Gly Tyr Ile Leu Ala Ser Ala Arg Leu Trp
385                 390                 395                 400
Glu Arg Leu Gly Gly Arg Ile Thr Val Leu Ser Ala Thr Leu Pro Arg
                405                 410                 415
Ala Leu Ala Asp Leu Phe Glu Ser Thr Leu Thr Ala Pro Ile Thr Phe
            420                 425                 430
Leu Asp Thr Pro Asp Leu Gly Leu Pro Ala Arg His Leu His Leu Thr
            435                 440                 445
Arg Gly His His Leu Thr Asp Pro Ala Thr Leu Glu Glu Ile Arg Leu
            450                 455                 460
Arg Leu Ser Arg Asp Glu Ser Val Leu Val Ile Ala Asn Asn Val Ser
465                 470                 475                 480
Gln Ala Ile Ala Leu Tyr Glu Gln Leu Ala Pro Asp Val Cys Glu Arg
                485                 490                 495
Phe Gly Gln Asp Ala Ala Leu Leu Leu His Ser Arg Phe Arg Arg Met
            500                 505                 510
Asp Arg Ser Arg Ile Glu Gln Lys Ile Ala Asp Arg Phe Ala Thr Val
            515                 520                 525
```

```
Ala Pro Asp Ala Gln Asn Ser Arg Lys Pro Gly Leu Val Val Ala Thr
        530                 535                 540

Gln Val Val Glu Val Ser Leu Asp Val Asp Phe Asp Val Leu Phe Thr
545                 550                 555                 560

Gly Ala Ala Pro Leu Glu Ala Leu Leu Gln Arg Phe Gly Arg Thr Asn
                565                 570                 575

Arg Val Gly Ala Arg Pro Pro Ala Asp Val Ile Val His His Pro Ala
            580                 585                 590

Trp Thr Thr Arg Arg Arg Gln Pro Gly Glu Tyr Ala Asp Gly Ile Tyr
        595                 600                 605

Pro Arg Glu Pro Val Glu Ser Ala Trp His Ile Leu Thr Arg Asn His
    610                 615                 620

Gly Arg Val Ile Asp Glu Ala Asp Ala Thr Ala Trp Leu Asp Glu Val
625                 630                 635                 640

Tyr Ala Thr Asp Trp Gly Arg Gln Trp His Arg Glu Val Leu Glu Arg
                645                 650                 655

Arg Glu Arg Phe Asp Arg Ala Phe Leu Gln Phe Arg Tyr Pro Phe Glu
            660                 665                 670

Asp Arg Thr Asp Leu Ala Asp Thr Phe Asp Glu Leu Phe Asp Gly Ser
        675                 680                 685

Glu Ala Ile Leu Ala Glu Asp Gln Asp Ala Tyr Ser Ala Ala Leu Ala
    690                 695                 700

Ala Pro Asp Gly Asp His Pro Gly Ala Gly Arg Leu Leu Ala Glu Glu
705                 710                 715                 720

Tyr Leu Ile Pro Val Pro His Trp Ala Ser Pro Leu Ser Arg Tyr Glu
                725                 730                 735

Lys Gln Leu Lys Val Arg Val Ile Asn Gly Asp Tyr His Pro Asp His
            740                 745                 750

Gly Leu Met Ala Val Arg Gly Leu Pro Gln Pro Ala Tyr Arg Ala Gly
        755                 760                 765

Glu Val Leu
    770

<210> SEQ ID NO 3
<211> LENGTH: 1144
<212> TYPE: DNA
<213> ORGANISM: Artificial Sequence
<220> FEATURE:
<223> OTHER INFORMATION: The sequence is synthetized.

<400> SEQUENCE: 3
atgagcgtgg tggttatgcc gatcgcgtca cactacgtct gaacgtcgaa aacccgaaac      60
tgtggagcgc cgaaatcccg aatctctatc gtgcggtggt tgaactgcac accgccgacg     120
gcacgctgat tgaagcagaa gcctgcgatg tcggtttccg cgaggtgcgg attgaaaatg     180
gtctgctgct gctgaacggc aagccgttgc tgattcgagg cgttaaccgt cacgagcatc     240
atcctctgca tggtcaggtc atggatgagc agacgatggt gcaggatatc ctgctgatga     300
agcagaacaa ctttaacgcc gtgcgctgtt cgcattatcc gaaccatccg ctgtggtaca     360
cgctgtgcga ccgctacggc ctgtatgtgg tggatgaagc caatattgaa acccacggca     420
tgggtttaca gggcggcttc gtctgggact gggtggatca gtcgctgatt aaatatgatg     480
aaaacggcaa cccgtggtcg gcttacggcg tgattttggc gatacgccg aacgatcgcc      540 agttctgtat gaacggtctg gtctttgccg accgcacgcc gcatccagcg ctgacggaag     600
```

```
caaaacacca gcagcagttt ttccagttcc gtttatccgg gcaaaccatc gaagtgacca    660
gcgaatacct gttccgtcat agcgataacg agctcctgca ctggatggtg gcgctggatg    720
gtaagccgct ggcaagcggt gaagtgcctc tggatgtcgc tccacaaggt aaacagttga    780
ttgaactgcc tgaactaccg cagccggaga gcgccgggca actctggctc acagtacgcg    840
tagtgcaacc gaacgcgacc gcatggtcag aagccgggca catcagcgcc tggcagcagt    900
ggcgtctggc ggaaaacctc agtgtgacgc tccccgccgc gtcccacgcc atcccgcatc    960
tgaccaccag cgaaatggat ttttgcatcg agctgggtaa taagcgttgg caatttaacc   1020
gccagtcagg ctttctttca cagatgtgga ttggcgataa aaaacaactg ctgacgccgc   1080
tgcgcgatca gttcacccgt gcaccgctgg ataacgacat tggcgtaagt gaagcgaccc   1140
gcat                                                                1144

<210> SEQ ID NO 4
<211> LENGTH: 222
<212> TYPE: DNA
<213> ORGANISM: Artificial Sequence
<220> FEATURE:
<223> OTHER INFORMATION: The sequence is synthetized.

<400> SEQUENCE: 4
ggctgcaggt cgactctaga ggatcctaat acgactcact atagggaata ttgtcctcat     60 cgcccttcg aggggtcgca acccgccgg tgcagtatga aggcggcgga gccgacacca    120
cggtcctcat cgcccttcg aggggtcgca acataaaacg aaaggctcag tcgaaagact    180
gggcctttcg ttttatgaat tcgtaatcat gtcatagctg tt                      222

<210> SEQ ID NO 5
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 5 acttttatt ttaggaggca aaagtgggcc gtctggacgc ggtgga                   46

<210> SEQ ID NO 6
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 6
aaataatctt catctaaaat atactttcac aagacctccc cggcgcggta              50

<210> SEQ ID NO 7
<211> LENGTH: 27
<212> TYPE: DNA
<213> ORGANISM: Artificial Sequence
<220> FEATURE:
<223> OTHER INFORMATION: The sequence is synthetized.

<400> SEQUENCE: 7
tacccaactt aatcgccttg cagcaca                                       27

<210> SEQ ID NO 8
<211> LENGTH: 28
<212> TYPE: DNA
<213> ORGANISM: Artificial Sequence
```

```
<220> FEATURE:
<223> OTHER INFORMATION: The sequence is synthetized.

<400> SEQUENCE: 8
ccgtcgatat tcagccatgt gccttctt                                          28

<210> SEQ ID NO 9
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 9
taccgcgccg gggaggtctt gtgaaagtat attttagatg aagattattt                  50

<210> SEQ ID NO 10
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 10
tccaccgcgt ccagacggcc cacttttgcc tcctaaaata aaaagt                      46

<210> SEQ ID NO 11
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 11
gtaaaacgac ggccagtgcc aagcttatga gcgtggtggt tatgcc                      46

<210> SEQ ID NO 12
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 12
acgaagccgc cctgtaaacc catgccgtgg gtttcaata                              39

<210> SEQ ID NO 13
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 13
tattgaaacc cacggcatgg gtttacaggg cggcttcgt                              39

<210> SEQ ID NO 14
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 14
tcgcgcgcgg ccgcggatcc tctagaatgc gggtcgcttc acttac                      46
```

<210> SEQ ID NO 15
<211> LENGTH: 1397
<212> TYPE: DNA
<213> ORGANISM: Artificial Sequence
<220> FEATURE:
<223> OTHER INFORMATION: The sequence is synthetized.

<400> SEQUENCE: 15

| gtgatggatt | taaaccacgg | aaaggcgttt | gcgccacaac | cggtcaaaac | atcttacgga | 60 |
| acatatgaag | actgcaagga | tgctgatatt | gtctgcattt | gcgccggagc | aaaccaaaaa | 120 |
| cctggtgaga | cacgccttga | attagtagaa | aagaacttga | agattttcaa | aggcatcgtt | 180 |
| agtgaagtca | tggcgagcgg | atttgacggc | attttcttag | tcgcgacaaa | tccggttgat | 240 |
| atcctgactt | acgcaacatg | gcgcgcctac | ctgtgacgga | agatcacttc | gcagaataaa | 300 |
| taaatcctgg | tgtccctgtt | gataccggga | agccctgggc | caacttttgg | cgaaaatgag | 360 |
| acgttgatcg | gcacgtaaga | ggttccaact | ttcaccataa | tgaaataaga | tcactaccgg | 420 |
| gcgtattttt | tgagttgtcg | agattttcag | gagctaagga | agctaaaatg | gagaaaaaaa | 480 |
| tcactggata | taccaccgtt | gatatatccc | aatggcatcg | taaagaacat | tttgaggcat | 540 |
| ttcagtcagt | tgctcaatgt | acctataacc | agaccgttca | gctggatatt | acggccttt | 600 |
| taaagaccgt | aaagaaaaat | aagcacaagt | tttatccggc | ctttattcac | attcttgccc | 660 |
| gcctgatgaa | tgctcatccg | gaattccgta | tggcaatgaa | agacggtgag | ctggtgatat | 720 |
| gggatagtgt | tcacccttgt | tacaccgttt | tccatgagca | aactgaaacg | ttttcatcgc | 780 |
| tctgagtga | ataccacgac | gatttccggc | agtttctaca | catatattcg | caagatgtgg | 840 |
| cgtgttacgg | tgaaaacctg | gcctatttcc | ctaaagggtt | tattgagaat | atgttttcg | 900 |
| tctcagccaa | tccctgggtg | agtttcacca | gttttgattt | aaacgtggcc | aatatggaca | 960 |
| acttcttcgc | ccccgttttc | accatgggca | aatattatac | gcaaggcgac | aaggtgctga | 1020 |
| tgccgctggc | gattcaggtt | catcatgccg | tctgtgatgg | cttccatgtc | ggcagaatgc | 1080 |
| ttaatgaatt | acaacagtac | tgcgatgagt | ggcagggcgg | ggcgtaaggc | gcgccattta | 1140 |
| aatgaagttc | ctattccgaa | gttcccgatg | cgtacaaaca | agaggagctg | gaccaaattg | 1200 |
| tagatgatgt | gaaaaacgca | gcttaccata | tcattgagaa | aaaaggcgcg | acttattatg | 1260 |
| gggttgcgat | gagtccttgct | cgcattacaa | aagccattct | tcataatgaa | acagcatat | 1320 |
| taactgtcag | cacatatttg | gacgggcaat | acggtgcaga | tgacgtgtac | atcggtgtgc | 1380 |
| cggctgtcgt | gaatcgc | | | | | 1397 |

<210> SEQ ID NO 16
<211> LENGTH: 291
<212> TYPE: DNA
<213> ORGANISM: Artificial Sequence
<220> FEATURE:
<223> OTHER INFORMATION: The sequence is synthetized.

<400> SEQUENCE: 16

| ggctgcaggt | cgactctaga | ggatcctaat | gtgagttagc | tcactcatta | ggcaccccag | 60 |
| gctttacact | ttatgcttcc | ggctcgtatg | ttgtgtggaa | ttgtgagcgg | ataacaagtc | 120 |
| ctcatcgccc | cttcgagggg | tcgcaacagc | ggcctgccaa | aagagcgggt | gattggaagc | 180 |
| ggcacaagtc | ctcatcgccc | cttcgagggg | tcgcaaccta | gcataacccc | ttggggcctc | 240 |
| taaacgggtc | ttgaggggtt | ttttggaatt | cgtaatcatg | tcatagctgt | t | 291 |

```
<210> SEQ ID NO 17
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 17
atgatgaaca aacatgtaa                                                19

<210> SEQ ID NO 18
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 18
ttagttgact ttttgttc                                                 18

<210> SEQ ID NO 19
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 19
taacaatttc acacaggaaa cagctgtggt cgccggtgcc ccgaac                  46

<210> SEQ ID NO 20
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 20
ttggcgggtg tcggggctgg cttaatcaca agacctcccc ggcgc                   45

<210> SEQ ID NO 21
<211> LENGTH: 47
<212> TYPE: DNA
<213> ORGANISM: Artificial Sequence
<220> FEATURE:
<223> OTHER INFORMATION: The sequence is synthetized.

<400> SEQUENCE: 21
gtaaaacgac ggccagtgcc aagcttcgat gagatggatt taaacca                 47

<210> SEQ ID NO 22
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 22
tttttctcaa cgagttcact atgttgcgta agtcaggata                         40

<210> SEQ ID NO 23
<211> LENGTH: 36
<212> TYPE: DNA
<213> ORGANISM: Artificial Sequence
<220> FEATURE:
<223> OTHER INFORMATION: The sequence is synthetized.
```

<400> SEQUENCE: 23
tatcctgact tacgcaacat ggcgcgccta cctgtg                                    36

<210> SEQ ID NO 24
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 24
cacaggtagg cgcgccatgt tgcgtaagtc aggata                                    36

<210> SEQ ID NO 25
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 25
tatcctgact tacgcaacat agtgaactcg ttgagaaaaa                                40

<210> SEQ ID NO 26
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 26
tcgcgcgcgg ccgcggatcc tctagagcga ttcacgacag cc                             42

<210> SEQ ID NO 27
<211> LENGTH: 807
<212> TYPE: DNA
<213> ORGANISM: Artificial Sequence
<220> FEATURE:
<223> OTHER INFORMATION: The sequence is synthetized.

<400> SEQUENCE: 27
cagccattcc attggagttt actccacaag atgatattgt tttgttggaa ccatatcatt          60
atttgggaaa aaatcctggt aaagaaattc gttcacaatt gattgaagcc tttaattatt         120
ggttggatgt taaaaagag gaccttgaag ttattcaaaa tgttgttggt atgttgcata          180
ctgcttcttt gctcatggat gatgttgaag atagttccgt tttacgtcgg ggttcaccag         240
ttgctcattt gatctacggt attccacaaa ctattaatac agccaattat gtttacttt          300 tagcctatca agaaattttt aaattgcgtc caacacctat tcctatgcca gttggtggtt         360
tgtttcgtat tgccgttcgt ttgatgatgg ccaaatctga atgtgatatt gattttgttc         420
aattagttaa tttgattagt atctatttc aaattcgtga tgattatatg aatcttcaat          480
ctagtgaata tgcacataac aaaaattttg ccgaggacct tactgaaggt aaattttcct         540
ttccaactat tcatagtatt catactaatc caagtagtcg tttagttatt aatacattac         600
agaaaaaatc tacatcccca gaatttttgc atcattgtgt taattatatg cgtactgaaa         660
cacattcctt tgaatatact cgtgaagttt tgaatacttt gtccggtgcc ttggaacgtg         720
aattgggtcg tttgcaagaa gaatttgccg aagctaatag tcgtatggat ttgggcgacg         780
ttgaatccga aggtcgtaca gggaaaa                                            807

<210> SEQ ID NO 28
<211> LENGTH: 406
<212> TYPE: DNA
<213> ORGANISM: Artificial Sequence
<220> FEATURE:
<223> OTHER INFORMATION: The sequence is synthetized.

<400> SEQUENCE: 28

```
cggaattctc tttgaaaaga taatgtatga ttatgctttc actcatattt atacagaaac    60
ttgatgtttt ctttcgagta tatacaaggt gattacatgt acgtttgaag tacaactcta   120
gattttgtag tgccctcttg ggctagcggt aaaggtgcgc attttttcac accctacaat   180
gttctgttca aaagattttg gtcaaacgct gtagaagtga agttggtgc gcatgtttcg   240
gcgttcgaaa cttctccgca gtgaaagata aatgatcgtc ctcatcgccc cttcgagggg   300
tcgcaactag tgcctcatct tcttcttcag catcctccga aaatggtgtc ctcatcgccc   360
cttcgagggg tcgcaacttt ttttgttttt tatgtctctc gagcgg              406
```

<210> SEQ ID NO 29
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 29

```
cagcatacac ctcactaggg tag                                            23
```

<210> SEQ ID NO 30
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 30

```
cccccttccag tgcattatgc aa                                            22
```

<210> SEQ ID NO 31
<211> LENGTH: 34
<212> TYPE: DNA
<213> ORGANISM: Artificial Sequence
<220> FEATURE:
<223> OTHER INFORMATION: The sequence is synthetized.

<400> SEQUENCE: 31

```
cccaagcttc agccattcca ttggagttta ctcc                                34
```

<210> SEQ ID NO 32
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 32

```
aacggcaata cgaaacaaac caccaactgg cataggaata ggtgttggac                50
```

<210> SEQ ID NO 33
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 33
gtccaacacc tattcctatg ccagttggtg gtttgtttcg tattgccgtt                50

<210> SEQ ID NO 34
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 34
cgcggatcct tttccctgta cgaccttcgg att                                  33

<210> SEQ ID NO 35
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 35
tatagggccg gtgaagtttt aagcagggct gaccccaag                            39

<210> SEQ ID NO 36
<211> LENGTH: 48
<212> TYPE: DNA
<213> ORGANISM: Artificial Sequence
<220> FEATURE:
<223> OTHER INFORMATION: The sequence is synthetized.

<400> SEQUENCE: 36
caacggcatc caatctaccc attttttcc cgggggatcc actagttc                   48

<210> SEQ ID NO 37
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 37
aaaaaaatgg gtagattgga tgccgttg                                        28

<210> SEQ ID NO 38
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 38
gtcagccctg cttaaaactt caccggccct atatgcag                             38

<210> SEQ ID NO 39
<211> LENGTH: 1972
<212> TYPE: DNA
<213> ORGANISM: Artificial Sequence
<220> FEATURE:
<223> OTHER INFORMATION: The sequence is synthetized.

<400> SEQUENCE: 39
tggcttgact aggggggtctt tgagttgctc atcaagatgg tcaggcattt atgaaaccct    60
gtttacatag taagaattat tttttaaaaa aactttccc tttttctttt ctgccatgaa     120
gtcacagaat gtcgttccac ccgggacgag ggtgtccccg aggacgagga ggacatggag   180

```
ccagaccctc agcaccatcc tttaggcccc aaaatctgag gctgcttcac cctcagcagc    240
ctcctgtgca atatcaatat gaacctccaa taagatacat tgatgagttt ggacaaacca    300
caactagaat gcagtgaaaa aaatgcttta tttgtgaaat ttgtgatgct attgctttat    360
ttgtaaccat tataagctgc aataaacaag ttggggtggg cgaagaactc cagcatgaga    420
tccccgcgct ggaggatcat ccagccggcg tcccggaaaa cgattccgaa gcccaacctt    480
tcatagaagg cggcggtgga atcgaaatct cgtagcacgt gctattcctt tgccctcgga    540
cgagtgctgg ggcgtcggtt tccactatcg gcgagtactt ctacacagcc atcggtccag    600
acggccgcgc ttctgcgggc gatttgtgta cgcccgacag tcccggctcc ggatcggacg    660
attgcgtcgc atcgaccctg cgcccaagct gcatcatcga aattgccgtc aaccaagctc    720
tgatagagtt ggtcaagacc aatgcggagc atatacgccc ggagccgcgg cgatcctgca    780
agctccggat gcctccgctc gaagtagcgc gtctgctgct ccatacaagc caaccacggc    840
ctccagaaga gatgttggc gacctcgtat tgggaatccc cgaacatcgc ctcgctccag    900
tcaatgaccg ctgttatgcg gccattgtcc gtcaggacat tgttggagcc gaaatccgcg    960
tgcacgaggt gccggacttc ggggcagtcc tcggcccaaa gcatcagctc atcgagagcc   1020
tgcgcgacgg acgcactgac ggtgtcgtcc atcacagttt gccagtgata cacatgggga   1080
tcagcaatcg cgcatatgaa atcacgccat gtagtgtatt gaccgattcc ttgcggtccg   1140
aatgggccga acccgctcgt ctggctaaga tcggccgcag cgatcgcatc catggcctcc   1200
gcgaccggct gcagaacagc gggcagttcg gtttcaggca ggtcttgcaa cgtgacaccc   1260
tgtgcacggc gggagatgca ataggtcagg ctctcgctga attccccaat gtcaagcact   1320
tccggaatcg ggagcgcggc cgatgcaaag tgccgataaa cataacgatc tttgtagaaa   1380
ccatcggcgc agctatttac ccgcaggaca tatccacgcc ctcctacatc gaagctgaaa   1440
gcacgagatt cttcgccctc cgagagctgc atcaggtcgg agacgctgtc gaacttttcg   1500
atcagaaact tctcgacaga cgtcgcggtg agttcaggct ttttcatcac gtgctgatca   1560
gatccgaaaa tggatataca agctcccggg agcttttttgc aaaagcctag gcctccaaaa   1620
aagcctcccc actacttctg gaatagctca gaggcagagg cggcctcggc ctctgcataa   1680
ataaaaaaaa ttagtcagcc atggggcgga gaatgggcgg aactgggcgg agttaggggc   1740
gggatgggcg gagttagggg cgggactatg gttgctgact aattgagatg cacagacttt   1800
gtacccttcc ccccacccat gcctccgtca gcgcaaggcc ctcttccccc ctgcccaatc   1860
aggccgcctt tccccaacca ccagatgagg caccccttcc cagttcctcc ttgtttttcct   1920 cccatgccac caccaatgcc ttgtcctaat aaccccccag tccctggggc ac            1972
```

<210> SEQ ID NO 40
<211> LENGTH: 166
<212> TYPE: DNA
<213> ORGANISM: Artificial Sequence
<220> FEATURE:
<223> OTHER INFORMATION: The sequence is synthetized.

<400> SEQUENCE: 40

```
taatacgact cactataggg aatattgtcc tcatcgcccc ttcgaggggt cgcaaccacc     60
actttctcaa actctccagc ccccaatttt ctgtcctcat cgccccttcg aggggtcgca    120
acataaaacg aaaggctcag tcgaaagact gggcctttcg ttttat                   166
```

<210> SEQ ID NO 41

```
<211> LENGTH: 16
<212> TYPE: DNA
<213> ORGANISM: Artificial Sequence
<220> FEATURE:
<223> OTHER INFORMATION: The sequence is synthetized.

<400> SEQUENCE: 41
accgcgcaca aggccc                                                     16

<210> SEQ ID NO 42
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 42
taagacagat gactgacatt ccacctaatt aatatccca                            39

<210> SEQ ID NO 43
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 43
tgcactccag cttagggaca gagt                                            24

<210> SEQ ID NO 44
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 44
caattaccat aacactaatt ttgtagtttc caatacactt agcct                     45

<210> SEQ ID NO 45
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 45
tggagcagct ttaaggaatg gtcgg                                           25

<210> SEQ ID NO 46
<211> LENGTH: 17
<212> TYPE: DNA
<213> ORGANISM: Artificial Sequence
<220> FEATURE:
<223> OTHER INFORMATION: The sequence is synthetized.

<400> SEQUENCE: 46
ctcgctcccg ccgatcc                                                    17

<210> SEQ ID NO 47
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 47
```

-continued acacaggaaa cagcttgcac tccagcttag ggacag          36

<210> SEQ ID NO 48
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 48
tttttcatca attaccataa cactaatttt gtagtttcca atacac          46

<210> SEQ ID NO 49
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 49
gtaattgatg aaaaagcctg aactcaccgc          30

<210> SEQ ID NO 50
<211> LENGTH: 29
<212> TYPE: DNA
<213> ORGANISM: Artificial Sequence
<220> FEATURE:
<223> OTHER INFORMATION: The sequence is synthetized.

<400> SEQUENCE: 50
ctgctccact attcctttgc cctcggacg          29

<210> SEQ ID NO 51
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 51
ggaatagtgg agcagcttta aggaatggtc g          31

<210> SEQ ID NO 52
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 52
tcggggctgg cttaactcgc tcccgccgat          30

<210> SEQ ID NO 53
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 53
gccgccgcga tcgccgtggg ccgtctggac          30

<210> SEQ ID NO 54
<211> LENGTH: 32
<212> TYPE: DNA

```
<213> ORGANISM: Artificial Sequence
<220> FEATURE:
<223> OTHER INFORMATION: The sequence is synthetized.

<400> SEQUENCE: 54
gcgttttttc ttgggtcaca agacctcccc gg                                  32
```